US009216276B2

(12) United States Patent
Slayton et al.

(10) Patent No.: US 9,216,276 B2
(45) Date of Patent: Dec. 22, 2015

(54) METHODS AND SYSTEMS FOR MODULATING MEDICANTS USING ACOUSTIC ENERGY

(75) Inventors: Michael H. Slayton, Tempe, AZ (US);
Peter G. Barthe, Phoenix, AZ (US);
Inder Raj S. Makin, Mesa, AZ (US)

(73) Assignee: Guided Therapy Systems, LLC, Mesa, AZ (US)

( * ) Notice: Subject to any disclaimer, the term of this patent is extended or adjusted under 35 U.S.C. 154(b) by 428 days.

(21) Appl. No.: 12/116,810

(22) Filed: May 7, 2008

(65) Prior Publication Data
US 2008/0281255 A1 Nov. 13, 2008

Related U.S. Application Data

(60) Provisional application No. 60/916,509, filed on May 7, 2007.

(51) Int. Cl.
*A61M 37/00* (2006.01)
*A61N 7/00* (2006.01)
(Continued)

(52) U.S. Cl.
CPC .......... *A61M 37/0092* (2013.01); *A61N 7/02* (2013.01); *A61B 8/4281* (2013.01);
(Continued)

(58) Field of Classification Search
CPC .............. A61N 2007/00; A61N 7/02; A61N 2007/004; A61N 2007/008; A61N 2007/0052; A61N 2007/0056; A61N 2007/006; A61N 2007/0065; A61N 2007/0069; A61N 2007/0073; A61N 2007/0078; A61N 2007/0082; A61N 2007/0086; A61N 2007/0091; A61N 2007/0095
USPC ........ 604/20, 22, 290; 601/2; 607/1–3, 61, 72
See application file for complete search history.

(56) References Cited

U.S. PATENT DOCUMENTS 2,427,348 A 9/1947 Bond et al.
3,913,386 A 10/1975 Saglio
(Continued)

FOREIGN PATENT DOCUMENTS

DE 4029175 3/1992
DE 10140064 3/2003
(Continued)

OTHER PUBLICATIONS

Husseini et al, "Investigating the mechanism of acoustically activated uptake of drugs from Pluronic micelles," BMC Cancer 2002, 2:20, Aug. 30, 2002, pp. 1-6.
(Continued)

*Primary Examiner* — Kevin C Sirmons
*Assistant Examiner* — William Carpenter
(74) *Attorney, Agent, or Firm* — Quarles & Brady, LLP

(57) ABSTRACT

This invention provides methods and systems uniquely capable of enhancing medicant delivery and/or effectiveness through the use of energy to predictably disrupt membranes and mechanically and thermally modulate cells and tissues. In exemplary embodiments, the methods and systems disclosed herein are capable of modulating multiple layers of tissue. In an exemplary embodiment, the energy is acoustic energy (e.g., ultrasound). In other exemplary embodiments, the energy is photon based energy (e.g., IPL, LED, laser, white light, etc.), or other energy forms, such radio frequency electric currents, or various combinations of acoustic energy, electromagnetic energy and other energy forms or energy absorbers such as cooling. Medicants can be first introduced to the region of interest by diffusion, circulation, and/or injection. An exemplary system for enhancing medicant delivery and/or effectiveness comprises a control system, a probe, and a display or indicator system. Imaging and/or monitoring may alternatively be coupled and/or co-housed with an ultrasound system contemplated by the present invention.

13 Claims, 12 Drawing Sheets

(51) Int. Cl.
*A61N 7/02* (2006.01)
*A61B 19/00* (2006.01)
*A61B 8/00* (2006.01)

(52) U.S. Cl.
CPC .............. *A61B 2019/5276* (2013.01); *A61M 2037/0007* (2013.01); *A61N 7/00* (2013.01); *A61N 2007/0008* (2013.01); *A61N 2007/0043* (2013.01); *A61N 2007/0056* (2013.01)

(56) References Cited

U.S. PATENT DOCUMENTS

| | | |
|---|---|---|
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto |
| 4,166,967 A | 9/1979 | Benes et al. |
| 4,211,948 A | 7/1980 | Smith et al. |
| 4,211,949 A | 7/1980 | Brisken et al. |
| 4,213,344 A | 7/1980 | Rose |
| 4,276,491 A | 6/1981 | Daniel |
| 4,315,514 A | 2/1982 | Drewes et al. |
| 4,325,381 A | 4/1982 | Glenn |
| 4,343,301 A | 8/1982 | Indech |
| 4,372,296 A | 2/1983 | Fahim |
| 4,379,145 A * | 4/1983 | Masuho et al. ............ 530/391.9 |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Taenzer |
| 4,431,008 A | 2/1984 | Wanner et al. |
| 4,441,486 A | 4/1984 | Pounds |
| 4,452,084 A | 6/1984 | Taenzer |
| 4,484,569 A | 11/1984 | Driller |
| 4,507,582 A | 3/1985 | Glenn |
| 4,513,749 A | 4/1985 | Kino |
| 4,513,750 A | 4/1985 | Heyman et al. |
| 4,527,550 A | 7/1985 | Ruggera et al. |
| 4,528,979 A | 7/1985 | Marchenko et al. |
| 4,534,221 A | 8/1985 | Fife et al. |
| 4,566,459 A | 1/1986 | Umemura et al. |
| 4,567,895 A | 2/1986 | Putzke |
| 4,586,512 A | 5/1986 | Do-Huu |
| 4,601,296 A | 7/1986 | Yerushalmi |
| 4,620,546 A | 11/1986 | Aida et al. |
| 4,637,256 A | 1/1987 | Sugiyama et al. |
| 4,646,756 A | 3/1987 | Watmough |
| 4,663,358 A | 5/1987 | Hyon |
| 4,668,516 A * | 5/1987 | Duraffourd et al. ............ 424/770 |
| 4,672,591 A | 6/1987 | Breimesser et al. |
| 4,680,499 A | 7/1987 | Umemura et al. |
| 4,697,588 A | 10/1987 | Reichenberger |
| 4,754,760 A | 7/1988 | Fukukita et al. |
| 4,757,820 A | 7/1988 | Itoh |
| 4,771,205 A | 9/1988 | Mequio |
| 4,801,459 A | 1/1989 | Liburdy |
| 4,803,625 A | 2/1989 | Fu et al. |
| 4,807,633 A | 2/1989 | Fry |
| 4,817,615 A | 4/1989 | Fukukita et al. |
| 4,858,613 A | 8/1989 | Fry |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,891,043 A | 1/1990 | Zeimer et al. |
| 4,893,624 A | 1/1990 | Lele |
| 4,896,673 A | 1/1990 | Rose |
| 4,900,540 A | 2/1990 | Ryan et al. |
| 4,901,729 A | 2/1990 | Saitoh et al. |
| 4,917,096 A | 4/1990 | Englehart et al. |
| 4,932,414 A | 6/1990 | Coleman et al. |
| 4,938,216 A | 7/1990 | Lele |
| 4,938,217 A * | 7/1990 | Lele ............................... 601/3 |
| 4,947,046 A | 8/1990 | Kawabata et al. |
| 4,951,653 A | 8/1990 | Fry et al. |
| 4,955,365 A | 9/1990 | Fry et al. |
| 4,958,626 A | 9/1990 | Nambu |
| 4,973,096 A | 11/1990 | Joyce |
| 4,976,709 A | 12/1990 | Sand |
| 4,979,501 A | 12/1990 | Valchanov |
| 4,992,989 A | 2/1991 | Watanabe et al. |
| 5,012,797 A | 5/1991 | Liang |
| 5,018,508 A | 5/1991 | Fry et al. |
| 5,030,874 A | 7/1991 | Saito et al. |
| 5,036,855 A | 8/1991 | Fry et al. |
| 5,040,537 A | 8/1991 | Katakura |
| 5,054,310 A | 10/1991 | Flynn |
| 5,054,470 A | 10/1991 | Fry et al. |
| 5,070,879 A | 12/1991 | Herres |
| 5,088,495 A | 2/1992 | Miyagawa |
| 5,115,814 A | 5/1992 | Griffith |
| 5,117,832 A | 6/1992 | Sanghvi et al. |
| 5,123,418 A | 6/1992 | Saurel |
| 5,143,063 A | 9/1992 | Fellner |
| 5,143,074 A | 9/1992 | Dory |
| 5,149,319 A | 9/1992 | Unger |
| 5,150,711 A | 9/1992 | Dory |
| 5,150,714 A | 9/1992 | Green |
| 5,152,294 A | 10/1992 | Mochizuki et al. |
| 5,156,144 A | 10/1992 | Iwasaki |
| 5,158,536 A | 10/1992 | Sekins |
| 5,159,931 A | 11/1992 | Pini |
| 5,163,421 A | 11/1992 | Bernstein et al. |
| 5,163,436 A | 11/1992 | Saitoh et al. |
| 5,178,135 A | 1/1993 | Uchiyama et al. |
| 5,190,518 A | 3/1993 | Takasu |
| 5,190,766 A | 3/1993 | Ishihara |
| 5,191,880 A | 3/1993 | McLeod |
| 5,205,287 A | 4/1993 | Erbel et al. |
| 5,209,720 A | 5/1993 | Unger |
| 5,212,671 A | 5/1993 | Fujii et al. |
| 5,215,680 A | 6/1993 | D'Arrigo |
| 5,224,467 A | 7/1993 | Oku |
| 5,230,334 A | 7/1993 | Klopotek |
| 5,230,338 A | 7/1993 | Allen et al. |
| 5,247,924 A | 9/1993 | Suzuki et al. |
| 5,255,681 A | 10/1993 | Ishimura et al. |
| 5,257,970 A | 11/1993 | Dougherty |
| 5,265,614 A | 11/1993 | Hayakawa |
| 5,267,985 A | 12/1993 | Shimada et al. |
| 5,269,297 A | 12/1993 | Weng et al. |
| 5,282,797 A | 2/1994 | Chess |
| 5,295,484 A | 3/1994 | Marcus |
| 5,295,486 A | 3/1994 | Wollschlager et al. |
| 5,304,169 A | 4/1994 | Sand |
| 5,305,756 A | 4/1994 | Entrekin et al. |
| 5,321,520 A | 6/1994 | Inga et al. |
| 5,323,779 A | 6/1994 | Hardy et al. |
| 5,327,895 A | 7/1994 | Hashimoto et al. |
| 5,348,016 A | 9/1994 | Unger et al. |
| 5,360,268 A | 11/1994 | Hayashi |
| 5,370,121 A | 12/1994 | Reichenberger |
| 5,371,483 A | 12/1994 | Bhardwaj |
| 5,375,602 A | 12/1994 | Lancee et al. |
| 5,379,773 A | 1/1995 | Hornsby |
| 5,380,280 A | 1/1995 | Peterson |
| 5,380,519 A | 1/1995 | Schneider et al. |
| 5,383,917 A | 1/1995 | Desai et al. |
| 5,391,140 A | 2/1995 | Schaetzle |
| 5,391,197 A | 2/1995 | Burdette et al. |
| 5,392,259 A | 2/1995 | Bolorforosh |
| 5,396,143 A | 3/1995 | Seyed-Bolorforosh et al. |
| 5,398,689 A | 3/1995 | Connor et al. |
| 5,406,503 A | 4/1995 | Williams, Jr. et al. |
| 5,417,216 A | 5/1995 | Tanaka |
| 5,419,327 A | 5/1995 | Rohwedder |
| 5,423,220 A | 6/1995 | Finsterwald et al. |
| 5,435,311 A | 7/1995 | Umemura |
| 5,438,998 A | 8/1995 | Hanafy |
| 5,458,596 A | 10/1995 | Lax |
| 5,460,179 A | 10/1995 | Okunuki et al. |

(56) References Cited

U.S. PATENT DOCUMENTS

| | | |
|---|---|---|
| 5,460,595 A * | 10/1995 | Hall et al. .................... 601/2 |
| 5,469,854 A | 11/1995 | Unger et al. |
| 5,471,488 A | 11/1995 | Bender |
| 5,487,388 A | 1/1996 | Rello et al. |
| 5,492,126 A | 2/1996 | Hennige et al. |
| 5,496,256 A | 3/1996 | Bock |
| 5,501,655 A | 3/1996 | Rolt et al. |
| 5,503,152 A | 4/1996 | Oakley et al. |
| 5,503,320 A | 4/1996 | Webster et al. |
| 5,507,790 A | 4/1996 | Weiss |
| 5,520,188 A | 5/1996 | Hennige |
| 5,522,869 A | 6/1996 | Burdette |
| 5,523,058 A | 6/1996 | Umemura et al. |
| 5,524,620 A | 6/1996 | Rosenschein |
| 5,524,624 A | 6/1996 | Tepper |
| 5,524,625 A | 6/1996 | Okazaki et al. |
| 5,526,624 A | 6/1996 | Berg |
| 5,526,812 A | 6/1996 | Dumoulin et al. |
| 5,526,814 A | 6/1996 | Cline et al. |
| 5,526,815 A | 6/1996 | Granz |
| 5,529,070 A | 6/1996 | Augustine et al. |
| 5,540,235 A | 7/1996 | Wilson |
| 5,558,092 A | 9/1996 | Unger |
| 5,560,362 A | 10/1996 | Sliwa et al. |
| 5,575,291 A | 11/1996 | Hayakawa |
| 5,575,807 A | 11/1996 | Faller |
| 5,577,502 A | 11/1996 | Darrow et al. |
| 5,577,507 A | 11/1996 | Snyder et al. |
| 5,577,991 A | 11/1996 | Akui et al. |
| 5,580,575 A | 12/1996 | Unger et al. |
| 5,601,526 A | 2/1997 | Chapelon |
| 5,603,323 A | 2/1997 | Pflugrath et al. |
| 5,609,562 A | 3/1997 | Kaali |
| 5,615,091 A | 3/1997 | Palatnik |
| 5,617,858 A | 4/1997 | Taverna et al. |
| 5,618,275 A | 4/1997 | Bock |
| 5,620,479 A | 4/1997 | Diederich |
| 5,622,175 A | 4/1997 | Sudol et al. |
| 5,638,819 A | 6/1997 | Manwaring et al. |
| 5,643,179 A | 7/1997 | Fujimoto |
| 5,644,085 A | 7/1997 | Lorraine et al. |
| 5,647,373 A | 7/1997 | Paltieli |
| 5,655,535 A | 8/1997 | Friemel et al. |
| 5,655,538 A | 8/1997 | Lorraine |
| 5,657,760 A | 8/1997 | Ying |
| 5,658,328 A | 8/1997 | Johnson |
| 5,660,836 A | 8/1997 | Knowlton |
| 5,662,116 A | 9/1997 | Kondo et al. |
| 5,665,053 A | 9/1997 | Jacobs |
| 5,665,141 A | 9/1997 | Vago |
| 5,671,746 A | 9/1997 | Dreschel et al. |
| 5,673,699 A | 10/1997 | Trahey et al. |
| 5,676,692 A | 10/1997 | Sanghvi et al. |
| 5,685,820 A | 11/1997 | Riek et al. |
| 5,687,737 A | 11/1997 | Branham et al. |
| 5,690,608 A | 11/1997 | Watanabe et al. |
| 5,694,936 A | 12/1997 | Fujimoto |
| 5,697,897 A | 12/1997 | Buchholtz |
| 5,701,900 A | 12/1997 | Shehada et al. |
| 5,704,361 A | 1/1998 | Seward et al. |
| 5,706,252 A | 1/1998 | Le Verrier et al. |
| 5,706,564 A | 1/1998 | Rhyne |
| 5,715,823 A | 2/1998 | Wood et al. |
| 5,720,287 A | 2/1998 | Chapelon et al. |
| 5,722,411 A | 3/1998 | Suzuki |
| 5,727,554 A | 3/1998 | Kalend et al. |
| 5,735,280 A | 4/1998 | Sherman et al. |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law et al. |
| 5,763,886 A | 6/1998 | Schulte |
| 5,769,790 A | 6/1998 | Watkins |
| 5,779,644 A | 7/1998 | Eberle et al. |
| 5,792,058 A | 8/1998 | Lee et al. |
| 5,795,297 A | 8/1998 | Daigle |
| 5,795,311 A | 8/1998 | Wess |
| 5,810,009 A | 9/1998 | Mine et al. |
| 5,810,888 A | 9/1998 | Fenn |
| 5,814,599 A * | 9/1998 | Mitragotri et al. ............. 514/7.4 |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle |
| 5,827,204 A | 10/1998 | Grandia et al. |
| 5,840,032 A | 11/1998 | Hatfield et al. |
| 5,844,140 A | 12/1998 | Seale |
| 5,853,367 A | 12/1998 | Chalek et al. |
| 5,869,751 A | 2/1999 | Bonin |
| 5,871,524 A | 2/1999 | Knowlton |
| 5,873,902 A | 2/1999 | Sanghvi et al. |
| 5,876,431 A | 3/1999 | Spehr et al. |
| 5,879,303 A | 3/1999 | Averkiou et al. |
| 5,882,557 A | 3/1999 | Hayakawa |
| 5,891,034 A | 4/1999 | Bucholz |
| 5,899,861 A | 5/1999 | Friemel et al. |
| 5,904,659 A | 5/1999 | Duarte et al. |
| 5,919,219 A | 7/1999 | Knowlton |
| 5,923,099 A | 7/1999 | Bilir |
| 5,924,989 A | 7/1999 | Polz |
| 5,928,169 A | 7/1999 | Schatzle et al. |
| 5,931,805 A | 8/1999 | Brisken |
| 5,938,606 A | 8/1999 | Bonnefous |
| 5,938,612 A | 8/1999 | Kline-Schoder |
| 5,948,011 A | 9/1999 | Knowlton |
| 5,957,844 A | 9/1999 | Dekel |
| 5,957,882 A | 9/1999 | Nita et al. |
| 5,957,941 A | 9/1999 | Ream |
| 5,967,980 A | 10/1999 | Ferre et al. |
| 5,968,034 A | 10/1999 | Fullmer et al. |
| 5,971,949 A | 10/1999 | Levin et al. |
| 5,977,538 A | 11/1999 | Unger et al. |
| 5,984,882 A | 11/1999 | Rosenschein et al. |
| 5,990,598 A | 11/1999 | Sudol et al. |
| 5,997,471 A | 12/1999 | Gumb et al. |
| 5,997,497 A | 12/1999 | Nita et al. |
| 5,999,843 A | 12/1999 | Anbar |
| 6,004,262 A | 12/1999 | Putz et al. |
| 6,007,499 A | 12/1999 | Martin et al. |
| 6,013,032 A | 1/2000 | Savord |
| 6,016,255 A | 1/2000 | Bolan et al. |
| 6,019,724 A | 2/2000 | Gronningsaeter et al. |
| 6,022,308 A | 2/2000 | Williams |
| 6,022,327 A | 2/2000 | Chang |
| 6,036,646 A | 3/2000 | Barthe |
| 6,039,048 A | 3/2000 | Silberg |
| 6,039,689 A | 3/2000 | Lizzi |
| 6,042,556 A | 3/2000 | Beach et al. |
| 6,049,159 A | 4/2000 | Barthe |
| 6,050,943 A | 4/2000 | Slayton et al. |
| 6,059,727 A | 5/2000 | Fowlkes |
| 6,071,239 A | 6/2000 | Cribbs et al. |
| 6,080,108 A | 6/2000 | Dunham |
| 6,083,148 A | 7/2000 | Williams |
| 6,086,535 A | 7/2000 | Ishibashi |
| 6,086,580 A | 7/2000 | Mordon et al. |
| 6,090,054 A | 7/2000 | Tagishi et al. |
| 6,093,883 A | 7/2000 | Sanghvi et al. |
| 6,101,407 A | 8/2000 | Groezinger |
| 6,106,469 A | 8/2000 | Suzuki et al. |
| 6,113,558 A | 9/2000 | Rosenschein et al. |
| 6,113,559 A | 9/2000 | Klopotek |
| 6,120,452 A | 9/2000 | Barthe |
| 6,123,081 A | 9/2000 | Durette |
| 6,126,619 A | 10/2000 | Peterson et al. |
| 6,135,971 A * | 10/2000 | Hutchinson et al. ............. 601/3 |
| 6,139,499 A | 10/2000 | Wilk |
| 6,159,150 A | 12/2000 | Yale et al. |
| 6,171,244 B1 | 1/2001 | Finger et al. |
| 6,176,840 B1 | 1/2001 | Nishimura et al. |

(56) References Cited

U.S. PATENT DOCUMENTS

| | | |
|---|---|---|
| 6,183,426 B1 | 2/2001 | Akisada et al. |
| 6,183,502 B1 | 2/2001 | Takeuchi |
| 6,183,773 B1 | 2/2001 | Anderson |
| 6,190,323 B1 | 2/2001 | Digs |
| 6,190,336 B1 | 2/2001 | Duarte et al. |
| 6,193,658 B1 | 2/2001 | Wendelken et al. |
| 6,210,327 B1 | 4/2001 | Brackett et al. |
| 6,213,948 B1 | 4/2001 | Barthe |
| 6,216,029 B1 | 4/2001 | Paltieli |
| 6,233,476 B1 | 5/2001 | Strommer et al. |
| 6,234,990 B1 | 5/2001 | Rowe et al. |
| 6,241,753 B1 | 6/2001 | Knowlton |
| 6,246,898 B1 | 6/2001 | Vesely et al. |
| 6,251,074 B1 | 6/2001 | Averkiou et al. |
| 6,251,088 B1 | 6/2001 | Kaufman et al. |
| 6,268,405 B1 | 7/2001 | Yao |
| 6,273,864 B1 | 8/2001 | Duarte et al. |
| 6,280,402 B1 | 8/2001 | Ishibashi et al. |
| 6,287,257 B1 | 9/2001 | Matichuk |
| 6,296,619 B1 | 10/2001 | Brisken |
| 6,301,989 B1 | 10/2001 | Brown et al. |
| 6,309,355 B1 | 10/2001 | Cain et al. |
| 6,311,090 B1 | 10/2001 | Knowlton |
| 6,315,741 B1 | 11/2001 | Martin |
| 6,322,509 B1 | 11/2001 | Pan et al. |
| 6,322,532 B1 | 11/2001 | D'Sa et al. |
| 6,325,540 B1 | 12/2001 | Lounsberry et al. |
| 6,325,758 B1 | 12/2001 | Carol et al. |
| 6,325,769 B1 | 12/2001 | Klopotek |
| 6,325,798 B1 | 12/2001 | Edwards et al. |
| 6,338,716 B1 | 1/2002 | Hossack et al. |
| 6,350,276 B1 | 2/2002 | Knowlton |
| 6,356,780 B1 | 3/2002 | Licato et al. |
| 6,361,531 B1 | 3/2002 | Hissong |
| 6,370,411 B1 | 4/2002 | Osadchy et al. |
| 6,375,672 B1 | 4/2002 | Aksan et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,390,982 B1 | 5/2002 | Bova et al. |
| 6,405,090 B1 | 6/2002 | Knowlton |
| 6,409,720 B1 | 6/2002 | Hissong |
| 6,413,216 B1 | 7/2002 | Cain et al. |
| 6,413,253 B1 | 7/2002 | Koop et al. |
| 6,413,254 B1 | 7/2002 | Hissong et al. |
| 6,419,648 B1 | 7/2002 | Vitek et al. |
| 6,423,007 B2 | 7/2002 | Lizzi et al. |
| 6,425,865 B1 | 7/2002 | Salcudean |
| 6,425,867 B1 | 7/2002 | Vaezy |
| 6,425,912 B1 | 7/2002 | Knowlton |
| 6,428,477 B1 | 8/2002 | Mason |
| 6,428,532 B1 | 8/2002 | Doukas et al. |
| 6,430,446 B1 | 8/2002 | Knowlton |
| 6,432,057 B1 | 8/2002 | Mazess et al. |
| 6,432,067 B1 | 8/2002 | Martin |
| 6,432,101 B1 | 8/2002 | Weber et al. |
| 6,436,061 B1 | 8/2002 | Costantino |
| 6,438,424 B1 | 8/2002 | Knowlton |
| 6,440,071 B1 | 8/2002 | Slayton |
| 6,440,121 B1 | 8/2002 | Weber et al. |
| 6,443,914 B1 | 9/2002 | Costantino |
| 6,453,202 B1 | 9/2002 | Knowlton |
| 6,461,378 B1 | 10/2002 | Knowlton |
| 6,470,216 B1 | 10/2002 | Knowlton |
| 6,488,626 B1 | 12/2002 | Lizzi et al. |
| 6,491,657 B2 | 12/2002 | Rowe et al. |
| 6,500,121 B1 | 12/2002 | Slayton |
| 6,500,141 B1 | 12/2002 | Irion et al. |
| 6,508,774 B1 | 1/2003 | Acker |
| 6,511,427 B1 | 1/2003 | Sliwa, Jr. et al. |
| 6,511,428 B1 | 1/2003 | Azuma |
| 6,514,244 B2 | 2/2003 | Pope |
| 6,517,484 B1 | 2/2003 | Wilk et al. |
| 6,524,250 B1 | 2/2003 | Weber |
| 6,540,679 B2 | 4/2003 | Slayton |
| 6,540,685 B1 | 4/2003 | Rhoads et al. |
| 6,540,700 B1 | 4/2003 | Fujimoto et al. |
| 6,554,771 B1 | 4/2003 | Buil et al. |
| 6,569,099 B1 | 5/2003 | Babaev |
| 6,569,108 B2 | 5/2003 | Sarvazyan et al. |
| 6,572,552 B2 | 6/2003 | Fukukita |
| 6,575,956 B1 | 6/2003 | Brisken et al. |
| 6,595,934 B1 | 7/2003 | Hissong et al. |
| 6,599,256 B1 | 7/2003 | Acker |
| 6,607,498 B2 | 8/2003 | Eshel |
| 6,618,620 B1 | 9/2003 | Freundlich et al. |
| 6,623,430 B1 * | 9/2003 | Slayton et al. ................ 600/439 |
| 6,626,854 B2 | 9/2003 | Friedman et al. |
| 6,626,855 B1 | 9/2003 | Weng et al. |
| 6,638,226 B2 | 10/2003 | He et al. |
| 6,645,162 B2 | 11/2003 | Friedman |
| 6,662,054 B2 | 12/2003 | Kreindel |
| 6,663,627 B2 | 12/2003 | Francischelli |
| 6,665,806 B1 | 12/2003 | Shimizu |
| 6,666,835 B2 | 12/2003 | Martin et al. |
| 6,669,638 B1 | 12/2003 | Miller et al. |
| 6,685,640 B1 | 2/2004 | Fry et al. |
| 6,692,450 B1 | 2/2004 | Coleman |
| 6,699,237 B2 | 3/2004 | Weber et al. |
| 6,716,184 B2 | 4/2004 | Vaezy et al. |
| 6,719,449 B1 | 4/2004 | Laughlin |
| 6,719,694 B2 | 4/2004 | Weng et al. |
| 6,726,627 B1 | 4/2004 | Lizzi et al. |
| 6,733,449 B1 | 5/2004 | Krishnamurthy et al. |
| 6,749,624 B2 | 6/2004 | Knowlton |
| 6,773,409 B2 | 8/2004 | Truckai et al. |
| 6,775,404 B1 | 8/2004 | Pagoulatos et al. |
| 6,790,187 B2 | 9/2004 | Thompson et al. |
| 6,824,516 B2 | 11/2004 | Batten et al. |
| 6,835,940 B2 | 12/2004 | Morikawa et al. |
| 6,846,290 B2 | 1/2005 | Lizzi et al. |
| 6,875,176 B2 | 4/2005 | Mourad et al. |
| 6,882,884 B1 | 4/2005 | Mosk et al. |
| 6,887,239 B2 | 5/2005 | Elstrom |
| 6,889,089 B2 | 5/2005 | Behl |
| 6,896,657 B2 | 5/2005 | Willis |
| 6,902,536 B2 | 6/2005 | Manna |
| 6,905,466 B2 | 6/2005 | Salgo et al. |
| 6,918,907 B2 | 7/2005 | Kelly |
| 6,920,883 B2 | 7/2005 | Bessette |
| 6,921,371 B2 | 7/2005 | Wilson |
| 6,932,771 B2 | 8/2005 | Whitmore |
| 6,932,814 B2 | 8/2005 | Wood |
| 6,936,044 B2 | 8/2005 | McDaniel |
| 6,936,046 B2 | 8/2005 | Hissong et al. |
| 6,945,937 B2 | 9/2005 | Culp et al. |
| 6,948,843 B2 | 9/2005 | Laugharn et al. |
| 6,953,941 B2 | 10/2005 | Nakano et al. |
| 6,958,043 B2 | 10/2005 | Hissong |
| 6,971,994 B1 | 12/2005 | Young et al. |
| 6,974,417 B2 | 12/2005 | Lockwood |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton et al. |
| 7,020,528 B2 | 3/2006 | Neev |
| 7,022,089 B2 | 4/2006 | Ooba et al. |
| 7,058,440 B2 | 6/2006 | Heuscher et al. |
| 7,063,666 B2 | 6/2006 | Weng et al. |
| 7,070,565 B2 | 7/2006 | Vaezy et al. |
| 7,074,218 B2 | 7/2006 | Washington et al. |
| 7,094,252 B2 | 8/2006 | Koop |
| 7,108,663 B2 | 9/2006 | Talish et al. |
| 7,115,123 B2 | 10/2006 | Knowlton |
| 7,122,029 B2 | 10/2006 | Koop et al. |
| 7,142,905 B2 | 11/2006 | Slayton |
| 7,165,451 B1 | 1/2007 | Brooks et al. |
| 7,179,238 B2 | 2/2007 | Hissong |
| 7,189,230 B2 | 3/2007 | Knowlton |
| 7,229,411 B2 | 6/2007 | Slayton |
| 7,235,592 B2 | 6/2007 | Muratoglu |
| 7,258,674 B2 | 8/2007 | Cribbs et al. |

(56) References Cited

U.S. PATENT DOCUMENTS

| | | |
|---|---|---|
| 7,273,459 B2 | 9/2007 | Desilets |
| 7,294,125 B2 | 11/2007 | Phalen et al. |
| 7,297,117 B2 | 11/2007 | Trucco et al. |
| 7,303,555 B2 | 12/2007 | Makin et al. |
| 7,327,071 B2 | 2/2008 | Nishiyama et al. |
| 7,331,951 B2 | 2/2008 | Eshel et al. |
| 7,332,985 B2 | 2/2008 | Larson, III et al. |
| 7,347,855 B2 | 3/2008 | Eshel |
| RE40,403 E | 6/2008 | Cho et al. |
| 7,393,325 B2 | 7/2008 | Barthe |
| 7,398,116 B2 | 7/2008 | Edwards |
| 7,399,279 B2 | 7/2008 | Abend et al. |
| 7,491,171 B2 | 2/2009 | Barthe et al. |
| 7,510,536 B2 | 3/2009 | Foley et al. |
| 7,530,356 B2 | 5/2009 | Slayton |
| 7,530,958 B2 | 5/2009 | Slayton |
| 7,571,336 B2 | 8/2009 | Barthe |
| 7,601,120 B2 | 10/2009 | Moilanen et al. |
| 7,615,015 B2 | 11/2009 | Coleman |
| 7,615,016 B2 | 11/2009 | Barthe |
| 7,686,763 B2 | 3/2010 | Vaezy et al. |
| 7,695,437 B2 | 4/2010 | Quistgaard et al. |
| 7,758,524 B2 | 7/2010 | Barthe |
| 7,789,841 B2 | 9/2010 | Huckle et al. |
| 7,824,348 B2 | 11/2010 | Barthe et al. |
| 7,846,096 B2 | 12/2010 | Mast et al. |
| 7,857,773 B2 | 12/2010 | Desilets et al. |
| 7,875,023 B2 | 1/2011 | Eshel et al. |
| 7,914,453 B2 | 3/2011 | Slayton et al. |
| 7,914,469 B2 | 3/2011 | Torbati |
| 7,931,611 B2 | 4/2011 | Novak et al. |
| 7,955,281 B2 | 6/2011 | Pedersen et al. |
| 7,967,764 B2 | 6/2011 | Lidgren et al. |
| 7,967,839 B2 | 6/2011 | Flock et al. |
| 8,057,389 B2 | 11/2011 | Barthe et al. |
| 8,057,465 B2 | 11/2011 | Sliwa, Jr. et al. |
| 8,066,641 B2 | 11/2011 | Barthe et al. |
| 8,123,707 B2 | 2/2012 | Huckle et al. |
| 8,128,618 B2 | 3/2012 | Gliklich et al. |
| 8,133,180 B2 | 3/2012 | Slayton et al. |
| 8,133,191 B2 | 3/2012 | Rosenberg et al. |
| 8,166,332 B2 | 4/2012 | Barthe et al. |
| 8,197,409 B2 | 6/2012 | Foley et al. |
| 8,206,299 B2 | 6/2012 | Foley et al. |
| 8,211,017 B2 | 7/2012 | Foley et al. |
| 8,262,591 B2 | 9/2012 | Pedersen et al. |
| 8,273,037 B2 | 9/2012 | Kreindel et al. |
| 8,282,554 B2 | 10/2012 | Makin et al. |
| 8,333,700 B1 | 12/2012 | Barthe et al. |
| 8,366,622 B2 | 2/2013 | Slayton et al. |
| 8,409,097 B2 | 4/2013 | Slayton et al. |
| 8,444,562 B2 | 5/2013 | Barthe et al. |
| 8,480,585 B2 | 7/2013 | Slayton et al. |
| 8,506,486 B2 | 8/2013 | Slayton et al. |
| 8,523,775 B2 | 9/2013 | Barthe et al. |
| 8,535,228 B2 | 9/2013 | Slayton et al. |
| 8,585,618 B2 | 11/2013 | Hunziker et al. |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,708,935 B2 | 4/2014 | Barthe et al. |
| 8,715,186 B2 | 5/2014 | Slayton et al. |
| 8,726,781 B2 | 5/2014 | Eckhoff et al. |
| 2001/0009997 A1 | 7/2001 | Pope |
| 2001/0009999 A1 | 7/2001 | Kaufman et al. |
| 2001/0014780 A1 | 8/2001 | Martin et al. |
| 2001/0014819 A1 | 8/2001 | Ingle et al. |
| 2001/0031922 A1 | 10/2001 | Weng et al. |
| 2001/0039380 A1 | 11/2001 | Larson et al. |
| 2001/0041880 A1 | 11/2001 | Brisken |
| 2002/0000763 A1 | 1/2002 | Jones |
| 2002/0002345 A1 | 1/2002 | Marlinghaus |
| 2002/0040199 A1* | 4/2002 | Klopotek ................ 601/3 |
| 2002/0040442 A1 | 4/2002 | Ishidera |
| 2002/0052550 A1 | 5/2002 | Madsen et al. |
| 2002/0055702 A1 | 5/2002 | Atala |
| 2002/0062077 A1 | 5/2002 | Emmenegger et al. |
| 2002/0062142 A1 | 5/2002 | Knowlton |
| 2002/0072691 A1 | 6/2002 | Thompson et al. |
| 2002/0082528 A1 | 6/2002 | Friedman et al. |
| 2002/0082529 A1 | 6/2002 | Suorsa et al. |
| 2002/0082589 A1 | 6/2002 | Friedman et al. |
| 2002/0087080 A1 | 7/2002 | Slayton et al. |
| 2002/0095143 A1 | 7/2002 | Key |
| 2002/0099094 A1 | 7/2002 | Anderson |
| 2002/0115917 A1 | 8/2002 | Honda et al. |
| 2002/0128648 A1 | 9/2002 | Weber |
| 2002/0143252 A1 | 10/2002 | Dunne et al. |
| 2002/0156400 A1 | 10/2002 | Babaev |
| 2002/0161357 A1 | 10/2002 | Anderson et al. |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1 | 11/2002 | Grunwald et al. |
| 2002/0193784 A1 | 12/2002 | McHale et al. |
| 2002/0193831 A1 | 12/2002 | Smith |
| 2003/0009153 A1 | 1/2003 | Brisken et al. |
| 2003/0014039 A1 | 1/2003 | Barzell et al. |
| 2003/0018255 A1 | 1/2003 | Martin |
| 2003/0028111 A1 | 2/2003 | Vaezy et al. |
| 2003/0028113 A1 | 2/2003 | Gilbert et al. |
| 2003/0032900 A1 | 2/2003 | Ella |
| 2003/0036706 A1 | 2/2003 | Slayton et al. |
| 2003/0040739 A1 | 2/2003 | Koop |
| 2003/0050678 A1 | 3/2003 | Sierra |
| 2003/0055417 A1 | 3/2003 | Truckai et al. |
| 2003/0060736 A1 | 3/2003 | Martin et al. |
| 2003/0065313 A1 | 4/2003 | Koop et al. |
| 2003/0074023 A1 | 4/2003 | Kaplan |
| 2003/0083536 A1 | 5/2003 | Eshel et al. |
| 2003/0092988 A1 | 5/2003 | Makin |
| 2003/0097071 A1 | 5/2003 | Halmann et al. |
| 2003/0099383 A1 | 5/2003 | Lefebvre |
| 2003/0125629 A1 | 7/2003 | Ustuner |
| 2003/0139790 A1 | 7/2003 | Ingle et al. |
| 2003/0171678 A1 | 9/2003 | Batten et al. |
| 2003/0171701 A1 | 9/2003 | Babaev |
| 2003/0176790 A1 | 9/2003 | Slayton |
| 2003/0191396 A1 | 10/2003 | Sanghvi et al. |
| 2003/0200481 A1 | 10/2003 | Stanley |
| 2003/0212129 A1* | 11/2003 | Liu et al. ................ 514/474 |
| 2003/0212351 A1 | 11/2003 | Hissong et al. |
| 2003/0212393 A1 | 11/2003 | Knowlton et al. |
| 2003/0216795 A1 | 11/2003 | Harth |
| 2003/0220536 A1 | 11/2003 | Hissong |
| 2003/0220585 A1 | 11/2003 | Hissong |
| 2003/0229331 A1 | 12/2003 | Brisken et al. |
| 2003/0233085 A1 | 12/2003 | Giammarusti |
| 2003/0236487 A1 | 12/2003 | Knowlton |
| 2004/0000316 A1 | 1/2004 | Knowlton et al. |
| 2004/0001809 A1 | 1/2004 | Brisken |
| 2004/0002705 A1 | 1/2004 | Knowlton et al. |
| 2004/0010222 A1 | 1/2004 | Nunomura et al. |
| 2004/0015106 A1 | 1/2004 | Coleman |
| 2004/0030227 A1 | 2/2004 | Littrup |
| 2004/0039312 A1 | 2/2004 | Hillstead et al. |
| 2004/0039418 A1 | 2/2004 | Elstrom et al. |
| 2004/0041563 A1 | 3/2004 | Lewin et al. |
| 2004/0042168 A1 | 3/2004 | Yang et al. |
| 2004/0044375 A1 | 3/2004 | Diederich et al. |
| 2004/0049134 A1 | 3/2004 | Tosaya et al. |
| 2004/0049734 A1 | 3/2004 | Simske |
| 2004/0059266 A1 | 3/2004 | Fry et al. |
| 2004/0068186 A1 | 4/2004 | Ishida et al. |
| 2004/0073079 A1 | 4/2004 | Altshuler et al. |
| 2004/0073113 A1 | 4/2004 | Salgo |
| 2004/0073115 A1 | 4/2004 | Horzewski et al. |
| 2004/0073116 A1 | 4/2004 | Smith |
| 2004/0073204 A1 | 4/2004 | Ryan et al. |

(56) References Cited

U.S. PATENT DOCUMENTS

| | | |
|---|---|---|
| 2004/0077977 A1 | 4/2004 | Ella et al. |
| 2004/0082857 A1 | 4/2004 | Schonenberger et al. |
| 2004/0082859 A1 | 4/2004 | Schaer |
| 2004/0102697 A1 | 5/2004 | Evron |
| 2004/0105559 A1 | 6/2004 | Aylward et al. |
| 2004/0122323 A1 | 6/2004 | Vortman et al. |
| 2004/0122493 A1 | 6/2004 | Ishibashi et al. |
| 2004/0143297 A1 | 7/2004 | Ramsey |
| 2004/0152982 A1 | 8/2004 | Hwang et al. |
| 2004/0158150 A1 | 8/2004 | Rabiner et al. |
| 2004/0186535 A1 | 9/2004 | Knowlton et al. |
| 2004/0189155 A1 | 9/2004 | Funakubo |
| 2004/0206365 A1 | 10/2004 | Knowlton |
| 2004/0210214 A1 | 10/2004 | Knowlton |
| 2004/0217675 A1 | 11/2004 | Desilets et al. |
| 2004/0249318 A1 | 12/2004 | Tanaka et al. |
| 2004/0254620 A1 | 12/2004 | Lacoste et al. |
| 2004/0267252 A1 | 12/2004 | Washington et al. |
| 2005/0033201 A1 | 2/2005 | Takahashi et al. |
| 2005/0033316 A1 | 2/2005 | Kertz |
| 2005/0038340 A1 | 2/2005 | Vaezy et al. |
| 2005/0055073 A1 | 3/2005 | Weber |
| 2005/0061834 A1 | 3/2005 | Garcia et al. |
| 2005/0070961 A1 | 3/2005 | Maki et al. |
| 2005/0074407 A1 | 4/2005 | Smith |
| 2005/0080469 A1 | 4/2005 | Larson |
| 2005/0091770 A1 | 5/2005 | Mourad et al. |
| 2005/0096542 A1 | 5/2005 | Weng et al. |
| 2005/0104690 A1 | 5/2005 | Larson, III et al. |
| 2005/0113689 A1 | 5/2005 | Gritzky |
| 2005/0134314 A1 | 6/2005 | Prather et al. |
| 2005/0137656 A1 | 6/2005 | Malak |
| 2005/0143677 A1 | 6/2005 | Young et al. |
| 2005/0154313 A1 | 7/2005 | Desilets et al. |
| 2005/0154314 A1 | 7/2005 | Quistgaard |
| 2005/0154332 A1 | 7/2005 | Zanelli |
| 2005/0154431 A1 | 7/2005 | Quistgaard |
| 2005/0187495 A1 | 8/2005 | Quistgaard et al. |
| 2005/0191252 A1 | 9/2005 | Mitsui |
| 2005/0193451 A1 | 9/2005 | Quistgaard et al. |
| 2005/0197681 A1 | 9/2005 | Barolet et al. |
| 2005/0228281 A1 | 10/2005 | Nefos |
| 2005/0240170 A1 | 10/2005 | Zhang et al. |
| 2005/0251120 A1 | 11/2005 | Anderson et al. |
| 2005/0256406 A1 | 11/2005 | Barthe |
| 2005/0261584 A1 | 11/2005 | Eshel et al. |
| 2005/0261585 A1 | 11/2005 | Makin et al. |
| 2005/0267454 A1 | 12/2005 | Hissong et al. |
| 2005/0288748 A1 | 12/2005 | Li et al. |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058671 A1 | 3/2006 | Vitek et al. |
| 2006/0058707 A1 | 3/2006 | Barthe |
| 2006/0058712 A1 | 3/2006 | Altshuler et al. |
| 2006/0074309 A1 | 4/2006 | Bonnefous |
| 2006/0074313 A1 | 4/2006 | Slayton et al. |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0094988 A1 | 5/2006 | Tosaya et al. |
| 2006/0111744 A1 | 5/2006 | Makin |
| 2006/0116583 A1 | 6/2006 | Ogasawara et al. |
| 2006/0116671 A1 | 6/2006 | Slayton |
| 2006/0122508 A1 | 6/2006 | Slayton |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0189972 A1 | 8/2006 | Grossman |
| 2006/0206105 A1 | 9/2006 | Chopra |
| 2006/0229514 A1 | 10/2006 | Wiener |
| 2006/0241440 A1 | 10/2006 | Eshel et al. |
| 2006/0241442 A1 | 10/2006 | Barthe |
| 2006/0241470 A1 | 10/2006 | Novak et al. |
| 2006/0250046 A1 | 11/2006 | Koizumi et al. |
| 2006/0282691 A1 | 12/2006 | Barthe |
| 2006/0291710 A1 | 12/2006 | Wang et al. |
| 2007/0032784 A1 | 2/2007 | Gliklich et al. |
| 2007/0035201 A1 | 2/2007 | Desilets et al. |
| 2007/0055154 A1 | 3/2007 | Torbati |
| 2007/0055155 A1 | 3/2007 | Owen et al. |
| 2007/0055156 A1 | 3/2007 | Desilets et al. |
| 2007/0065420 A1 | 3/2007 | Johnson |
| 2007/0083120 A1 | 4/2007 | Cain et al. |
| 2007/0087060 A1 | 4/2007 | Dietrich |
| 2007/0088245 A1 | 4/2007 | Babaev et al. |
| 2007/0088346 A1 | 4/2007 | Mirizzi et al. |
| 2007/0161902 A1 | 7/2007 | Dan |
| 2007/0166357 A1 | 7/2007 | Shaffer et al. |
| 2007/0167709 A1 | 7/2007 | Slayton |
| 2007/0208253 A1 | 9/2007 | Slayton |
| 2007/0219604 A1 | 9/2007 | Yaroslavsky et al. |
| 2007/0219605 A1 | 9/2007 | Yaroslavsky et al. |
| 2007/0238994 A1 | 10/2007 | Stecco et al. |
| 2007/0239075 A1 | 10/2007 | Rosenberg et al. |
| 2007/0239079 A1 | 10/2007 | Manstein et al. |
| 2007/0239142 A1 | 10/2007 | Altshuler et al. |
| 2008/0027328 A1 | 1/2008 | Klopotek et al. |
| 2008/0039724 A1 | 2/2008 | Seip et al. |
| 2008/0071255 A1 | 3/2008 | Barthe |
| 2008/0086054 A1 | 4/2008 | Slayton |
| 2008/0097253 A1 | 4/2008 | Pederson |
| 2008/0139974 A1 | 6/2008 | Da Silva |
| 2008/0146970 A1 | 6/2008 | Litman et al. |
| 2008/0167556 A1 | 7/2008 | Thompson et al. |
| 2008/0183077 A1 | 7/2008 | Moreau-Gobard et al. |
| 2008/0188745 A1 | 8/2008 | Chen et al. |
| 2008/0195000 A1 | 8/2008 | Spooner et al. |
| 2008/0200810 A1 | 8/2008 | Buchalter |
| 2008/0200813 A1 | 8/2008 | Quistgaard |
| 2008/0214966 A1 | 9/2008 | Slayton |
| 2008/0221491 A1 | 9/2008 | Slayton |
| 2008/0223379 A1 | 9/2008 | Stuker et al. |
| 2008/0243035 A1 | 10/2008 | Crunkilton |
| 2008/0269608 A1 | 10/2008 | Anderson et al. |
| 2008/0275342 A1 | 11/2008 | Barthe |
| 2008/0281206 A1 | 11/2008 | Bartlett et al. |
| 2008/0281236 A1 | 11/2008 | Eshel et al. |
| 2008/0281237 A1 | 11/2008 | Slayton |
| 2008/0281255 A1 | 11/2008 | Slayton |
| 2008/0294073 A1 | 11/2008 | Barthe |
| 2008/0319356 A1 | 12/2008 | Cain et al. |
| 2009/0005680 A1 | 1/2009 | Jones et al. |
| 2009/0012394 A1 | 1/2009 | Hobelsberger et al. |
| 2009/0043198 A1 | 2/2009 | Milner et al. |
| 2009/0043293 A1 | 2/2009 | Pankratov et al. |
| 2009/0069677 A1 | 3/2009 | Chen et al. |
| 2009/0093737 A1 | 4/2009 | Chomas et al. |
| 2009/0156969 A1 | 6/2009 | Santangelo |
| 2009/0171252 A1 | 7/2009 | Bockenstedt et al. |
| 2009/0177122 A1 | 7/2009 | Peterson |
| 2009/0177123 A1 | 7/2009 | Peterson |
| 2009/0182231 A1 | 7/2009 | Barthe et al. |
| 2009/0216159 A1 | 8/2009 | Slayton et al. |
| 2009/0226424 A1 | 9/2009 | Hsu |
| 2009/0227910 A1 | 9/2009 | Pedersen et al. |
| 2009/0253988 A1 | 10/2009 | Slayton et al. |
| 2009/0299175 A1 | 12/2009 | Bernstein et al. |
| 2009/0318909 A1 | 12/2009 | Debenedictis et al. |
| 2010/0011236 A1 | 1/2010 | Barthe et al. |
| 2010/0022919 A1 | 1/2010 | Peterson |
| 2010/0022922 A1 | 1/2010 | Barthe et al. |
| 2010/0042020 A1 | 2/2010 | Ben-Ezra |
| 2010/0049178 A1 | 2/2010 | Deem et al. |
| 2010/0063422 A1 | 3/2010 | Hynynen et al. |
| 2010/0130891 A1 | 5/2010 | Taggart et al. |
| 2010/0160782 A1 | 6/2010 | Slayton et al. |

(56) References Cited

U.S. PATENT DOCUMENTS

| | | | |
|---|---|---|---|
| 2010/0160837 A1 | 6/2010 | Hunziker et al. |
| 2010/0168576 A1 | 7/2010 | Poland et al. |
| 2010/0191120 A1 | 7/2010 | Kraus et al. |
| 2010/0241035 A1 | 9/2010 | Barthe et al. |
| 2010/0280420 A1 | 11/2010 | Barthe et al. |
| 2010/0286518 A1 | 11/2010 | Lee et al. |
| 2011/0040171 A1 | 2/2011 | Foley et al. |
| 2011/0040190 A1 | 2/2011 | Jahnke et al. |
| 2011/0087099 A1 | 4/2011 | Eshel et al. |
| 2011/0087255 A1 | 4/2011 | Mccormack et al. |
| 2011/0112405 A1 | 5/2011 | Barthe et al. |
| 2011/0178444 A1 | 7/2011 | Slayton et al. |
| 2011/0190745 A1 | 8/2011 | Uebelhoer et al. |
| 2011/0264012 A1 | 10/2011 | Lautzenhiser et al. |
| 2012/0004549 A1 | 1/2012 | Barthe et al. |
| 2012/0016239 A1 | 1/2012 | Barthe et al. |
| 2012/0029353 A1 | 2/2012 | Slayton et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0111339 A1 | 5/2012 | Barthe et al. |
| 2012/0143056 A1 | 6/2012 | Slayton et al. |
| 2012/0165668 A1 | 6/2012 | Slayton et al. |
| 2012/0165848 A1 | 6/2012 | Slayton et al. |
| 2012/0197120 A1 | 8/2012 | Makin et al. |
| 2012/0197121 A1 | 8/2012 | Slayton et al. |
| 2012/0215105 A1 | 8/2012 | Slayton et al. |
| 2012/0271294 A1 | 10/2012 | Barthe et al. |
| 2012/0296240 A1 | 11/2012 | Azhari et al. |
| 2012/0316426 A1 | 12/2012 | Foley et al. |
| 2012/0330197 A1 | 12/2012 | Makin et al. |
| 2012/0330222 A1 | 12/2012 | Barthe et al. |
| 2012/0330223 A1 | 12/2012 | Makin et al. |
| 2013/0012755 A1 | 1/2013 | Slayton |
| 2013/0012816 A1 | 1/2013 | Slayton et al. |
| 2013/0012838 A1 | 1/2013 | Jaeger et al. |
| 2013/0012842 A1 | 1/2013 | Barthe |
| 2013/0018286 A1 | 1/2013 | Slayton et al. |
| 2013/0046209 A1 | 2/2013 | Slayton et al. |
| 2013/0066208 A1 | 3/2013 | Barthe et al. |
| 2013/0066237 A1 | 3/2013 | Smotrich et al. |
| 2013/0072826 A1 | 3/2013 | Slayton et al. |
| 2013/0096471 A1 | 4/2013 | Slayton et al. |
| 2013/0190659 A1 | 7/2013 | Slayton et al. |
| 2013/0211258 A1 | 8/2013 | Barthe et al. |
| 2013/0281853 A1 | 10/2013 | Slayton et al. |
| 2013/0281891 A1 | 10/2013 | Slayton et al. |
| 2013/0296697 A1 | 11/2013 | Slayton et al. |
| 2013/0296700 A1 | 11/2013 | Slayton et al. |
| 2013/0303904 A1 | 11/2013 | Barthe et al. |
| 2013/0303905 A1 | 11/2013 | Barthe et al. |
| 2013/0310863 A1 | 11/2013 | Barthe et al. |
| 2014/0082907 A1 | 3/2014 | Barthe |
| 2014/0142430 A1 | 5/2014 | Slayton et al. |
| 2014/0148834 A1 | 5/2014 | Barthe et al. |
| 2014/0180174 A1 | 6/2014 | Slayton et al. |
| 2014/0187944 A1 | 7/2014 | Slayton et al. |
| 2014/0188015 A1 | 7/2014 | Slayton et al. |
| 2014/0188145 A1 | 7/2014 | Slayton et al. |

FOREIGN PATENT DOCUMENTS

| | | |
|---|---|---|
| DE | 10219217 | 11/2003 |
| DE | 10219297 | 11/2003 |
| DE | 20314479 | 3/2004 |
| EP | 0344773 | 12/1989 |
| EP | 1479412 | 11/1991 |
| EP | 0473553 | 4/1992 |
| EP | 0661029 | 7/1995 |
| EP | 1050322 | 11/2000 |
| EP | 1234566 | 8/2002 |
| EP | 1262160 | 12/2002 |
| EP | 1374944 A | 1/2004 |
| GB | 2113099 | 8/1983 |
| JP | 63036171 | 2/1988 |
| JP | 03048299 | 3/1991 |
| JP | 3123559 | 5/1991 |
| JP | 03136642 | 6/1991 |
| JP | 4089058 | 3/1992 |
| JP | 04150847 | 5/1992 |
| JP | 7080087 | 3/1995 |
| JP | 07505793 | 6/1995 |
| JP | 7222782 | 8/1995 |
| JP | 09047458 | 2/1997 |
| JP | 11505440 | 5/1999 |
| JP | 11506636 | 6/1999 |
| JP | 2000166940 | 6/2000 |
| JP | 2001170068 | 6/2001 |
| JP | 2002078764 | 3/2002 |
| JP | 2002515786 | 5/2002 |
| JP | 2002521118 | 7/2002 |
| JP | 2002537939 | 11/2002 |
| JP | 2003050298 | 2/2003 |
| JP | 2003204982 | 7/2003 |
| JP | 2004147719 | 5/2004 |
| JP | 2005503388 | 2/2005 |
| JP | 2005527336 | 9/2005 |
| JP | 2005323213 | 11/2005 |
| JP | 2006520247 | 9/2006 |
| JP | 2007505793 A | 3/2007 |
| JP | 2009518126 | 5/2009 |
| JP | 2010517695 | 5/2010 |
| KR | 1020010024871 | 3/2001 |
| KR | 100400870 B1 | 10/2003 |
| KR | 1020060113930 | 11/2006 |
| KR | 1020070065332 | 6/2007 |
| KR | 1020070070161 | 7/2007 |
| KR | 1020070098856 | 10/2007 |
| KR | 1020070104878 | 10/2007 |
| KR | 1020070114105 | 11/2007 |
| WO | 9625888 | 8/1996 |
| WO | 9639079 A1 | 12/1996 |
| WO | 9735518 | 10/1997 |
| WO | WO9735518 | 10/1997 |
| WO | 9832379 | 7/1998 |
| WO | WO9832379 | 7/1998 |
| WO | 9933520 | 7/1999 |
| WO | WO9933520 | 7/1999 |
| WO | 9949788 | 10/1999 |
| WO | WO9949788 | 10/1999 |
| WO | 0006032 | 2/2000 |
| WO | 0015300 | 3/2000 |
| WO | WO0015300 | 3/2000 |
| WO | 0021612 | 4/2000 |
| WO | WO0021612 | 4/2000 |
| WO | 0053113 | 9/2000 |
| WO | 0128623 | 4/2001 |
| WO | 0209813 | 4/2001 |
| WO | WO0128623 | 4/2001 |
| WO | 0182777 | 11/2001 |
| WO | 0182778 | 11/2001 |
| WO | 0187161 | 11/2001 |
| WO | WO0182777 | 11/2001 |
| WO | WO0182778 | 11/2001 |
| WO | WO0187161 | 11/2001 |
| WO | 0209813 | 2/2002 |
| WO | 0224050 | 3/2002 |
| WO | WO0209813 | 3/2002 |
| WO | WO0224050 | 3/2002 |
| WO | 02092168 A | 11/2002 |
| WO | 020292168 | 11/2002 |
| WO | WO02092168 | 11/2002 |
| WO | 03053266 A | 7/2003 |
| WO | 03065347 | 8/2003 |
| WO | 03070105 | 8/2003 |
| WO | 03077833 | 8/2003 |
| WO | WO03070105 | 8/2003 |
| WO | WO03077833 | 9/2003 |
| WO | 03086215 | 10/2003 |
| WO | WO03086215 | 10/2003 |
| WO | 03096883 | 11/2003 |
| WO | 03099177 | 12/2003 |

(56) References Cited

FOREIGN PATENT DOCUMENTS

| WO | 03101530 | | 12/2003 |
|---|---|---|---|
| WO | 2004000116 | A | 12/2003 |
| WO | WO03099177 | | 12/2003 |
| WO | 2004080147 | | 9/2004 |
| WO | 2004110558 | | 12/2004 |
| WO | 2005011804 | A | 2/2005 |
| WO | 2005065408 | | 7/2005 |
| WO | 2005090978 | | 9/2005 |
| WO | 2006036870 | | 4/2006 |
| WO | 2006042163 | A | 4/2006 |
| WO | 2006042168 | | 4/2006 |
| WO | 2006042201 | | 4/2006 |
| WO | 2006065671 | | 6/2006 |
| WO | 2006082573 | | 8/2006 |
| WO | 2007067563 | A | 6/2007 |
| WO | 2008024923 | A2 | 2/2008 |
| WO | 2008036622 | A | 3/2008 |
| WO | 2009013729 | | 1/2009 |
| WO | 2009149390 | A1 | 12/2009 |
| WO | 2014055708 | A1 | 4/2014 |

OTHER PUBLICATIONS

Barthe et al, "Ultrasound therapy system and ablation results utilizing miniature imaging/therapy arrays," Ultrasonics Symposium, 2004 IEEE, Aug. 23, 2004, pp. 1792-1795, vol. 3.

Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.

Makin et al, "Confirmal Bulk Ablation and Therapy Monitoring Using Intracorporeal Image-Treat Ultrasound Arrays," 4th International Symposium on Theraputic Ultrasound, Sep. 19, 2004.

Mast et al, "Bulk Ablation of Soft Tissue with Intense Ultrasound: Modeling and Experiments," J. Acoust. Soc. Am., Oct. 1, 2005, pp. 2715-2724, vol. 118(4).

Samir Mitragotri, "Healing sound: the use of ultrasound in drug delivery and other therapeutic applications," Nature Reviews: Drug Delivery, pp. 255-260, vol. 4.

Makin et al, "Miniaturized Ultrasound Arrays for Interstitial Ablation and Imaging," UltraSound Med. Biol. 2005, Nov. 1, 2005, pp. 1539-1550, vol. 31(11).

White et al "Selective Creating of Thermal Injury Zones in the Superficial Musculoaponeurotic System Using Intense Ultrasound Therapy," Arch Facial Plastic Surgery, Jan./Feb. 2007, vol. 9, No. 1.

Gliklich et al, "Clinical Pilot Study of Intense Ultrasound Therapy to Deep Dermal Facial Skin and Subcutaneous Tissues," Arch Facial Plastic Surgery, Mar. 1, 2007, vol. 9, No. 1.

International Search Report and Written Opinion dated Aug. 12, 2008.

Written Opinion dated Aug. 12, 2008 for PCT/US2008/062930.

International Preliminary Report on Patentability for International application No. PCT/US2008/062930 dated Nov. 19, 2009.

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.

Wasson, Scott, "NVIDIA's GeFroce 7800 GTX graphics processor Power MADD," http://techreport.com/reviews/2005q2/geforce-7800gtx/index.x?pg=1, Jun. 22, 2005, 4 pages.

Coon, Joshua et al., "Protein identification using sequential ion/ion reactions and tandem mass spectometry" Proceedings of the National Academy of Sciences of the USA, vol. 102, No. 27, Jul. 5, 2005, pp. 9463-9468.

Corry, Peter M., et al., "Human Cancer Treatment with Ultrasound", IEEE Transactions on Sonics and Ultrasonics, vol. SU-31, No. 5, Sep. 1984, pp. 444,456.

Daum et al., "Design and Evaluation of a Feedback Based Phased Array System for Ultrasound Surgery," IEEE Transactions on Ultrasonics, Feroelectronics, and Frequency Control, vol. 45, No. 2, Mar. 1998, pp. 431-438.

Davis, Brian J., et al., "An Acoustic Phase Shift Technique for the Non-Invasive Measurement of Temperature Changes in Tissues", 1985 Ultrasonics Symposium, pp. 921-924.

Sassen, Sander, "ATI's R520 architecture, the new king of the hill?" http://www.hardwareanalysis.com/content/article/1813, Sep. 16, 2005, 2 pages.

Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.

Hassan et al., "Structure and Morphology of Freeze/Thawed PVA Hydrogels," Macromolecules, Mar. 11, 2000, pp. 2472-2479, vol. 33, No. 7.

Wang, H., et al., "Limits on Focused Ultrasound for Deep Hyperthermia", 1994 Ultrasonic Symposium, Nov. 1-4, 1994, pp. 1869-1872, vol. 3.

Jenne, J., et al., "Temperature Mapping for High Energy US-Therapy", 1994 Ultrasonics Symposium, pp. 1879-1882.

Johnson, S.A., et al., "Non-Intrusive Measurement of Microwave and Ultrasound-Induced Hyperthermia by Acoustic temperature Tomography", Ultrasonics Symposium Proceedings, pp. 977-982.

Syka J. E. P. et al., "Peptide and Protein Sequence Analysis by Electron Transfer Dissociation Mass Spectometry," Proceedings of the National Academy of Sciences of USA, National Academy of Aceince, Washington, DC, vol. 101, No. 26, Jun. 29, 2004, pp. 9528-9533.

Surry et al., "Poly(vinyl alcohol) cryogel phantoms for use in ultrasound and MR imaging," Phys. Med. Biol., Dec. 6, 2004, pp. 5529-5546, vol. 49.

Smith, Nadine Barrie, et al., "Non-Invasive In Vivo Temperature Mapping of Ultrasound Heating Using Magnetic Resonance Techniques", 1994 Ultrasonics Symposium, pp. 1829-1832, vol. 3.

Manohar et al, "Photoacoustic mammography laboratory prototype: imaging of breast tissue phantoms," Journal of Biomedical Optics, Nov./Dec. 2004, pp. 1172-1181, vol. 9, No. 6.

Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.

Paradossi et al., "Poly(vinyl alcohol) as versatile biomaterial for potential biomedical applications," Journal of Materials Science: Materials in Medicine, 2003, pp. 687-691, vol. 14.

Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.

Righetti et al, "Elastographic Characterization of HIFU-Induced Lesions in Canine Livers," 1999, Ultrasound in Med & Bio, vol. 25, No. 7, pp. 1099-1113.

Seip, Ralf, et al., "Noninvasive Detection of Thermal Effects Due to Highly Focused Ultrasonic Fiels," IEEE Symposium, pp. 1229-1232, vol. 2, Oct. 3-Nov. 1993.

Sanghvi, N. T., et al., "Transrectal Ablation of Prostate Tissue Using Focused Ultrasound," 1993 Ultrasonics Symposium, IEEE, pp. 1207-1210.

Chen, L. et al., ""Effect of Blood Perfusion on the ablation of liver perenchyma with high intensity focused ultrasound,"" Phys. Med. Biol; 38:1661-1673; 1993b.

Damianou et al., Application of the Thermal Dose Concept for Predicting the Necrosed Tissue Volume During Ultrasound Surgery, 1993 IEEE Ultrasound Symposium, pp. 1199-1202.

Fry, W.J. et al., "Production of Focal Destructive Lesions in the Central Nervous System with Ultrasound," J. Neurosurg., 11:471-478; 1954.

Harr, G.R. et al., "Tissue Destruction with Focused Ultrasound in Vivo," Eur. Urol. 23 (suppl. 1):8-11; 1993.

Jeffers et al., "Evaluation of the Effect of Cavitation Activity on Drug-Ultrasound Synergisms," 1993 IEEE Ultrasonics Symposium, pp. 925-928.

Madersbacher, S. et al., "Tissue Ablation in Bening Prostatic Hyperplasia with High Intensity Focused Ultrasound," Dur. Urol., 23 (suppl. 1):39-43; 1993.

(56) References Cited

OTHER PUBLICATIONS

Saad et al., "Ultrasound-Enhanced Effects of Adriamycin Against Murine Tumors," Ultrasound in Med. & Biol. vol. 18, No. 8, pp. 715-723 (1992).
Simon et al., "Applications of Lipid-Coated Microbubble Ultrasonic Contrast to Tumor Therapy," Ultrasound in Med. & Biol. vol. 19, No. 2, pp. 123-125 (1993).
Talbert, D. G., "An Add-On Modification for Linear Array Real-Time Ultrasound Scanners to Produce 3D Displays," UTS Int'l 1977 Brighton, England (Jun. 28-30, 1977) pp. 57-67.
Tata et al., "Interaction of Ultrasound and Model Membrane Systems: Analyses and Predictions," American Chemical Society, Phys. Chem. 1992, 96, pp. 3548-3555.
Arthur et al., "Non-invasive estimation of hyperthermia temperatures with ultrasound," Int. J. Hyperthermia, Sep. 2005, 21(6), pp. 589-600.
Husseini et al, "The Role of Cavitation in Acoustically Activated Drug Delivery," J. Control Release, Oct. 3, 2005, pp. 253-261, vol. 107(2).
Mitragotri, Samir; "Healing sound: the use of ultrasound in drug delivery and other therapeutic applications," Nature Reviews; Drug Delivery, pp. 255-260, vol. 4.
PCT/US2012/046122 International Search Report Jan. 30, 2013.
PCT/US2012/046123 International Search Report Jan. 28, 2013.
PCT/US2012/046125 International Search Report Jan. 28, 2013.
Ueno, S., et al., "Ultrasound Thermometry in Hyperthermia", 1990 Ultrasonic Symposium, pp. 1645-1652.
European Examination Report in related Application No. 05808908.7 dated Jun. 29, 2009.
European Examination Report in related Application No. 05810308.6 dated Jun. 29, 2009.
European Examination Report in related Application No. 10185100.4 dated Jan. 6, 2014.
European Examination Report in related Application No. 10185120.2 dated Jan. 22, 2014.
Decision of the Korean Intellectrual Property Tribunal dated Jun. 28, 2013 regarding Korean Patent No. 10-1142108, which is related to the pending application and/or an application identified in the Table on the pp. 2-5 of the information Disclosure Statement herein (English translation, English translation certification, and Korean decision included).
International Search Report and Written Opinion dated Jan. 23, 2014 in Application No. PCT/US2012/046122.
International Search Report and Written Opinion dated Jan. 23, 2014 in Application No. PCT/US2012/046123.
International Search Report and Written Opinion dated Jan. 28, 2012 in Application No. PCT/US2012/046327.
International Search Report and Written Opinion dated Jan. 28, 2013 in Application No. PCT/US2012/046125.
International Search Report and Written Opinion dated Feb. 14, 2013 in Application No. PCT/US2011/001361.
International Search Report and Written Opinion dated Feb. 14, 2013 in Application No. PCT/US2011/001362.
International Search Report and Written Opinion dated Feb. 14, 2013 in Application No. PCT/US2011/001366.
International Search Report and Written Opinion dated Apr. 6, 2012 in Application No. PCT/US2011/001367.
European Examination Report in related Application No. 09835856.7 dated Apr. 11, 2014.
Calderhead et al., One Mechanism Behind LED Photo-Therapy for Wound Healing and Skin Rejuvenation: Key Role of the Mast Cell, Laser Therapy, 2008, 17(3): 141-148.
International Preliminary Report on Patentability in Application No. PCT/US2011/001366 dated Feb. 14, 2013.
PCT International Search Report and Written Opinion, PCT/US2014/030779, Sep. 1, 2014, 8 pages.
European Patent Office, Examination Report, EP 07814933.3, Aug. 5, 2014, 5 pages.
European Patent Office, Examination Report, EP 05798870.1, Oct. 20, 2014, 5 pages.
European Patent Office, Examination Report, EP 10185100.4, Oct. 24, 2014, 4 pages.
European Patent Office, Examination Report, EP 10185112.9, Oct. 24, 2014, 5 pages.
European Patent Office, Examination Report, EP 10185117.8, Oct. 24, 2014, 5 pages.
European Patent Office, Examination Report, EP 10185120.2, Oct. 24, 2014, 4 pages.

\* cited by examiner

METHODS AND SYSTEMS FOR MODULATING MEDICANTS USING ACOUSTIC ENERGY

CROSS-REFERENCE TO RELATED APPLICATIONS

This application claims the benefit of U.S. Provisional Patent Application Ser. No. 60/916,509, entitled METHOD AND SYSTEM FOR ULTRASOUND TREATMENT TO ENHANCE MEDICANTS, filed May 7, 2007, which is incorporated by reference herein in its entirety.

BACKGROUND OF THE INVENTION

Skin comprises at least four distinct layers of tissue: the nonviable epidermis (i.e., the stratum corneum), the viable epidermis, the dermis, and subcutaneous connective tissue and fat. The circulatory system lies in the dermis and tissues below the dermis. As skin generally prohibits the transport of macromolecules to the dermis and tissues below the dermis, needles are often required to administer macromolecular medicants.

Ultrasound has long been used for diagnostic imaging applications. More recently however, several new therapeutic applications for ultrasound are being discovered. Among the applications for ultrasound, enhanced transdermal medicant delivery and/or effectiveness has received considerable attention. To date, however, the better part of ultrasound-enhanced medicant delivery and/or effectiveness efforts have been focused on ultrasound at frequencies below 200 kHz, and prior systems have directed ultrasound at single layers of tissue.

SUMMARY OF THE INVENTION

This invention improves upon the prior art by providing methods and systems uniquely capable of enhancing medicant delivery and/or effectiveness through the use of energy (e.g., acoustic energy). An exemplary embodiment predictably disrupts membranes and mechanically and thermally modulates cells and tissues. In exemplary embodiments, the methods and systems disclosed herein are capable of modulating multiple layers of tissue (e.g., a plurality of depths within a cell membrane or tissue).

The methods and systems disclosed herein contemplate delivering focused, unfocused, and/or defocused ultrasound energy to a region of interest at various spatial and temporal energy settings, in the range of about 100 kHz to about 500 MHz. In an exemplary embodiment, the energy is acoustic energy (e.g., ultrasound). In other exemplary embodiments, the energy is photon based energy (e.g., IPL, LED, laser, white light, etc.), or other energy forms, such radio frequency electric currents, or various combinations of acoustic energy, electromagnetic energy and other energy forms or energy absorbers such as cooling.

Medicants can be first introduced to the region of interest by diffusion, circulation, and/or injection, to name a few. In other embodiments, the methods and systems disclosed herein are configured to interact with chemicals naturally occurring or already existing within the body in terms of, for example, concentration, function, and cell division properties.

An exemplary system for enhancing medicant delivery and/or effectiveness comprises a control system, a probe, and a display or indicator system. The probe can comprise various probe and/or transducer configurations. In an exemplary embodiment, the probe delivers focused, unfocused, and/or defocused ultrasound energy to the region of interest. Imaging and/or monitoring may alternatively be coupled and/or co-housed with an ultrasound system contemplated by the present invention.

The control system and display system can also comprise various configurations for controlling probe and system functionality, including for example, a microprocessor with software and a plurality of input/output devices, a system for controlling electronic and/or mechanical scanning and/or multiplexing of transducers, a system for power delivery, systems for monitoring, systems for sensing the spatial position of the probe and/or transducers, and systems for handling user input and recording treatment results, among others.

In accordance with an exemplary embodiment, a coupling agent, comprised of at least one of a gel, cream, liquid, emulsion or other compound, is used to couple the probe to a patient's body. In an exemplary embodiment, the coupling agent contains medicants that are delivered to the patient's body during the emission of energy from the probe.

BRIEF DESCRIPTION OF THE DRAWINGS

The subject matter of the invention is particularly pointed out and distinctly claimed in the concluding portion of the specification. The invention, however, both as to structure and method of operation, may best be understood by reference to the following description taken in conjunction with the claims and the accompanying drawing figures, in which like parts may be referred to by like numerals, and:

DETAILED DESCRIPTION

Figure 1A:
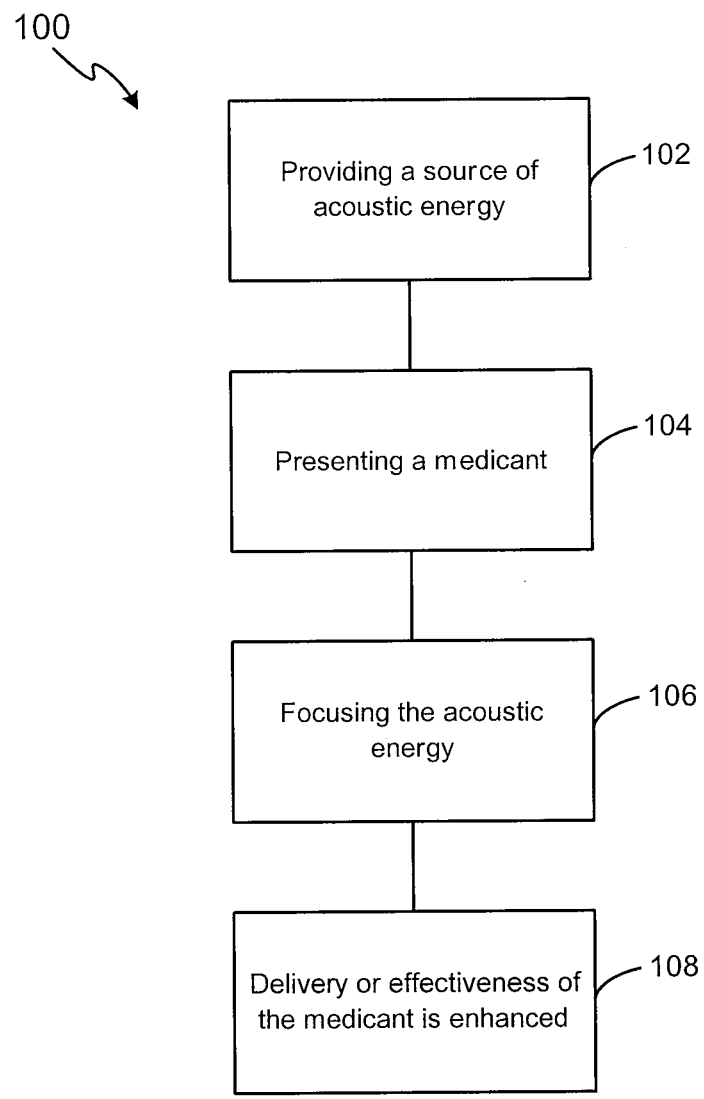
FIG. 1A illustrates a block diagram of a method for modulating medicants in accordance with an exemplary embodiment of the present invention.

The present invention may be described herein in terms of various functional components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical contexts and the exemplary embodiments relating to methods and systems for using acoustic energy to enhance medicant delivery and effectiveness, as described herein, are merely indicative of exemplary applications for the invention. For example, the principles, features and methods discussed may be applied to any medical application, e.g., the methods and systems described herein can be used in combination with any coagulative therapies. Further, various aspects of the present invention may be suitably applied to other applications.

Disclosed is an exemplary method of modulating cells and tissues to enhance medicant delivery and/or effectiveness that comprises delivering energy to a region of interest (ROI) within one or more layers of tissue. In an exemplary embodiment, the energy is acoustic energy (e.g., ultrasound in the range of about 100 kHz to about 500 MHz, more preferably in the range of about 100 kHz to about 20 MHz, and most preferably in the range of about 200 kHz to about 20 MHz). In other exemplary embodiments, the energy is photon based energy (e.g., IPL, LED, laser, white light, etc.), or other energy forms, such radio frequency electric currents, or various combinations of acoustic energy, electromagnetic energy and other energy forms or energy absorbers such as cooling. In yet other exemplary embodiments, combinations of acoustic and photon based energy sources can be used, e.g., pre-treating with photon-based energy and then use of ultrasound energy alone or simultaneously with the photon-based energy, or any other combinations for modulating cells and tissues to enhance medicant delivery and/or effectiveness.

An exemplary method of modulating cells and tissues produces numerous predictable mechanical and thermal physiological effects at a ROI. For example, an exemplary method is predictable in terms of precision and accuracy in targeting and focusing energy at desired three dimensional coordinates within a cell membrane or tissue or a plurality of cell membranes and tissues and at various spatial and temporal energy settings. For example, because cells are on the order of micrometers, and cell membrane thickness is on the order of nanometers, to target an individual cell or membrane would require a very high or extreme frequency, thus a plurality is useful in exemplary embodiments. In an exemplary embodiment ultrasound, photon based or radio frequency (electromagnetic) treatment is provided to artificial or engineered tissues, such as artificial skin or organs, or stem cell derived tissues.

Providing ultrasound energy to cell membranes or tissues can enhance drug delivery and/or effectiveness in numerous ways. For example, the permeability and/or transparency of cell membranes can be modulated. For example, in some embodiments, the permeability and/or transparency of cell membranes is increased. Heating can cause better diffusion of drugs through the layers of skin tissue. Cavitation and radiation force involves sustained oscillatory motion of bubbles (aka stable cavitation) and/or rapid growth and collapse of bubbles (aka inertial cavitation). Resulting fluid velocities, shear forces and shock waves can disrupt cell membranes or tissues and induce chemical changes in the surrounding medium. The collapse of bubbles can additionally increase the bubble core temperature and induce chemical changes in the medium (e.g., generate highly reactive species, such as free radicals). Each of the above effects can impact drug delivery and effectiveness. In addition, other ways to impact drug delivery include melting or mechanically disrupting thermally sensitive or mechanically fragile medicant-carrying liposomes and/or other chemical loaded, gas or liquid filled stabilized spheres, analogous to local delivery.

For example, drug delivery can be enhanced when shock waves generated upon collapse of bubbles disrupt the stratum corneum and thereby enhance skin permeability. Likewise, drug effectiveness can be enhanced when shock waves transiently compromise the integrity of cell membranes or tissues, or when local free-radical concentration enhances medicant toxicity. Moreover, certain medicants can be activated and/or released using energy. In that regard, a medicant encapsulated in a carrier can be released at the site of interest using energy (e.g., acoustic energy). Consider for example, U.S. Pat. No. 6,623,430, entitled "Method and Apparatus for Safely Delivering Medicants to a Region of Tissue Using Imaging, Therapy and Temperature Monitoring Ultrasonic System", and co-pending U.S. patent application Ser. No. 08/943,728, entitled "Method and Apparatus for Safely Delivering Medicants to a Region of Tissue Using Ultrasound", both of which are hereby incorporated by reference.

In various exemplary embodiments, the ROI is located within one of the nonviable epidermis (i.e., the stratum corneum), the viable epidermis, the dermis, the subcutaneous connective tissue and fat, and the muscle. Depths may be in the range of about 0 mm to about 60 mm, 80 mm, or 100 mm or more. In accordance with an exemplary embodiment, the ROI is located about 20 mm to about 30 mm below the stratum corneum. Further, while only one ROI is depicted, a plurality of ROI can be treated, and in some embodiments, simultaneously. For example, the ROI may consist of one or more organs or a combination of tissues either superficial or deep within the body.

This method and system is uniquely capable of disrupting cell membranes or tissues and inducing chemical changes in the surrounding medium at either a single or multiple layers of skin tissue simultaneously (e.g., a plurality of depths within a cell membrane or tissue simultaneously). For example, one frequency of acoustic energy at one skin layer might generate shock waves upon collapse of bubbles to disrupt the stratum corneum and thereby enhance skin permeability. A different frequency of acoustic energy at a different skin layer might simply provide heat to cause better diffusion of medicants through the layers of skin tissue. Yet another frequency of acoustic energy at a different skin layer might compromise the integrity of cell membranes or tissues, or generate local free-radicals to enhance or reduce medicant toxicity. In an exemplary embodiment, acoustic energy is deposited in three-dimensions and at variable depths to selectively increase tissue permeability to thereby steer or guide the medicant through the tissue to a region of interest.

For example, and with reference to FIG. 1A, an exemplary embodiment provides a method 100 for enhancing medicant delivery and/or effectiveness comprising the steps of: providing a source of acoustic energy 102; presenting a medicant to a cell membrane or tissue 104; and focusing the acoustic energy from the source to a plurality of depths within the cell membrane or tissue 106, wherein the acoustic energy is in the range of about 100 kHz to about 500 MHz, wherein the plurality of depths are each in the range of about 0 mm to about 100 mm; and wherein the delivery and/or effectiveness of the medicant is enhanced 108.

Yet another exemplary embodiment provides a method for delivering a medicant to a region of interest within a cell membrane or tissue comprising the steps of: providing a source of acoustic energy; presenting a medicant to the cell membrane or tissue; focusing the acoustic energy from the source to a first depth within the cell membrane or tissue, wherein the acoustic energy has a first spatial and temporal energy profile; and focusing the acoustic energy from the source to a second depth within the cell membrane or tissue, wherein the acoustic energy has a second spatial and temporal energy profile; and wherein the medicant is delivered to the region of interest.

Medicants can be first introduced to a region of interest orally, by diffusion upon application to the skin, circulation following entry into the circulatory system, direct injection thereto, to name a few. That said, introduction may occur either in or not in direct contact with the circulatory system. For example, in some exemplary embodiments, the methods and systems disclosed herein affect chemicals naturally occurring or already existing within the body (e.g., cells, amino acids, proteins, antibodies, minerals, vitamins, etc.) in terms of, for example, concentration, function, and cell division properties. In one exemplary embodiment, the method and system disclosed herein "spur" or catalyze cellular processes, for example cell growth.

In accordance with exemplary embodiments, a coupling agent, comprised of at least one of a gel, cream, liquid, emulsion solid, composite or other compound, is used to couple the probe to a patient's body. In an exemplary embodiment, the coupling agent contains medicants that are delivered to the patient's body during the emission of energy from the probe.

In accordance with an aspect of an exemplary embodiment, the medicant is also used to couple a probe to the skin. Therefore, the medicant can have multiple uses. First, the medicant is used to couple the probe to the skin. Second, since the medicant contains drugs and other medicines, the same are delivered to the skin when energy is applied from the probe (e.g, via sonophoresis).

In an exemplary embodiment, the medicines and drugs within the medicant are used for skin treatment. Therefore, as the patient is being treated by the application of energy at non-ablative levels, therapeutic drugs are also being administered to the patient to treat skin disorders.

Figure 1B:
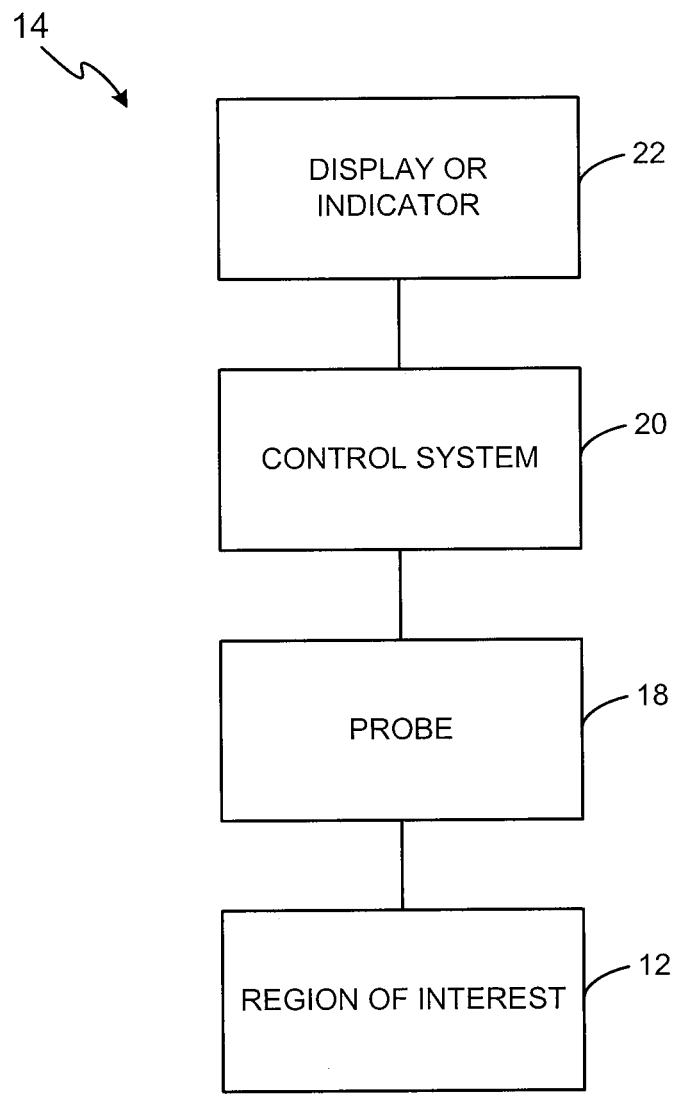
FIG. 1B illustrates a block diagram of a system for modulating medicants in accordance with an exemplary embodiment of the present invention.

An exemplary system 14 for modulating cells and tissues to enhance medicant delivery and/or effectiveness is provided and depicted in FIG. 1B. An exemplary system 14 comprises a display or indicator 22, a control system 20, and a probe 18.

Display system can be any type of system that conveys images or information apart from images about system 14 or ROI 12 to the user. Therefore, display system 22 can be a computer monitor, television screen or it can be a simply type of indicator system such a liquid crystal display or light emitting diode display in various exemplary embodiments. Liquid crystal displays and light emitting diode displays are particularly useful when system 14 is a hand-held system.

Figure 2:
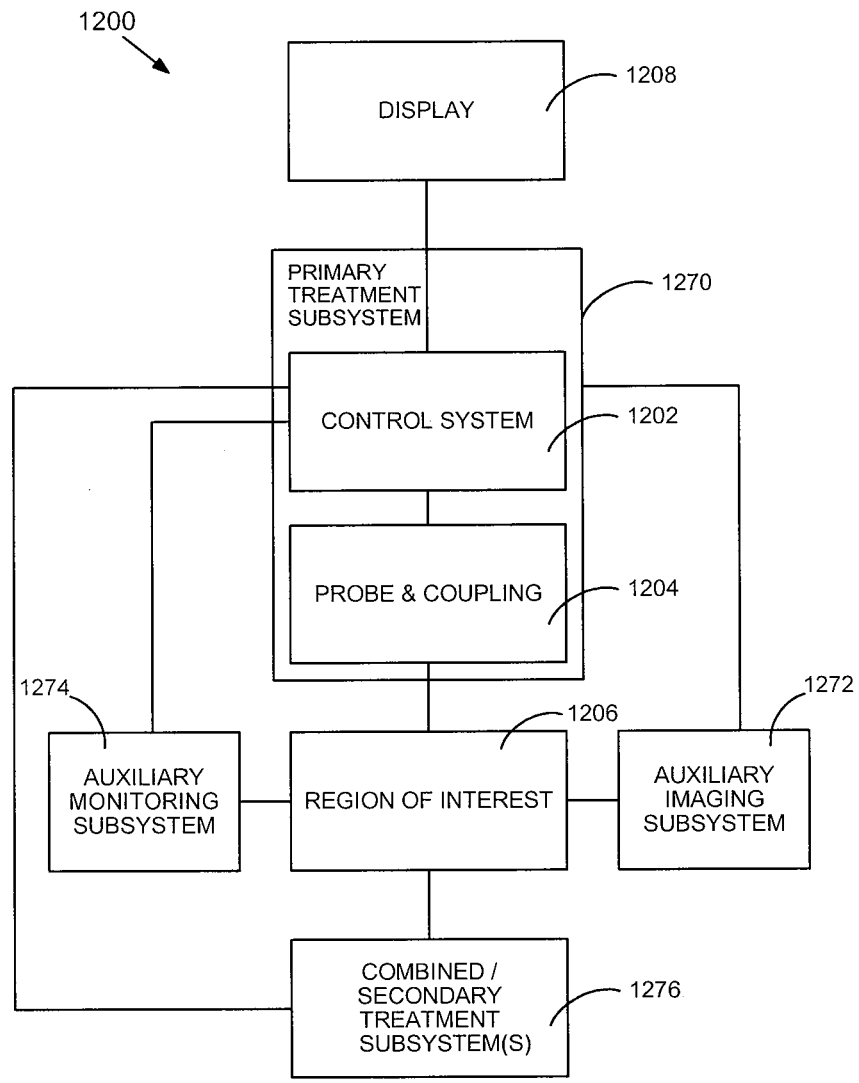
FIG. 2 illustrates a block diagram of a treatment system comprising an ultrasound treatment subsystem combined with additional subsystems and methods of treatment monitoring and/or treatment imaging as well as a secondary treatment subsystem in accordance with an exemplary embodiment of the present invention.

In accordance with another exemplary embodiment, with reference to FIG. 2, an exemplary treatment system 1200 can be configured with and/or combined with various auxiliary systems to provide additional functions. For example, an exemplary treatment system 1200 for treating a region of interest 1206 can comprise a control system 1202, a probe 1204, and a display 1208. Treatment system 1200 further comprises one or more of an auxiliary imaging modality 1274 and/or one or more of an auxiliary monitoring or sensing modality 1272, which may be based upon at least one of photography and other visual optical methods, magnetic resonance imaging (MRI), computed tomography (CT), optical coherence tomography (OCT), electromagnetic, microwave, or radio frequency (RF) methods, positron emission tomography (PET), infrared, ultrasound, acoustic, or any other suitable method of visualization, localization, or monitoring within region-of-interest 1206, including imaging/monitoring enhancements. Such imaging/monitoring enhancement for ultrasound imaging via probe 1204 and control system 1202 could comprise M-mode, persistence, filtering, color, Doppler, and harmonic imaging among others; furthermore an ultrasound treatment system 1270, as a primary source of treatment, may be combined with a secondary source of treatment 1276, including radio frequency (RF) energy, microwave energy, or other photon based energy methods including intense pulsed light (IPL), laser, infrared laser, microwave, or any other suitable energy source. A multi-modality coupler analogous to FIG. 1B is a particularly useful embodiment for a multi-modality treatment, sensing, monitoring and imaging system.

Figure 3:
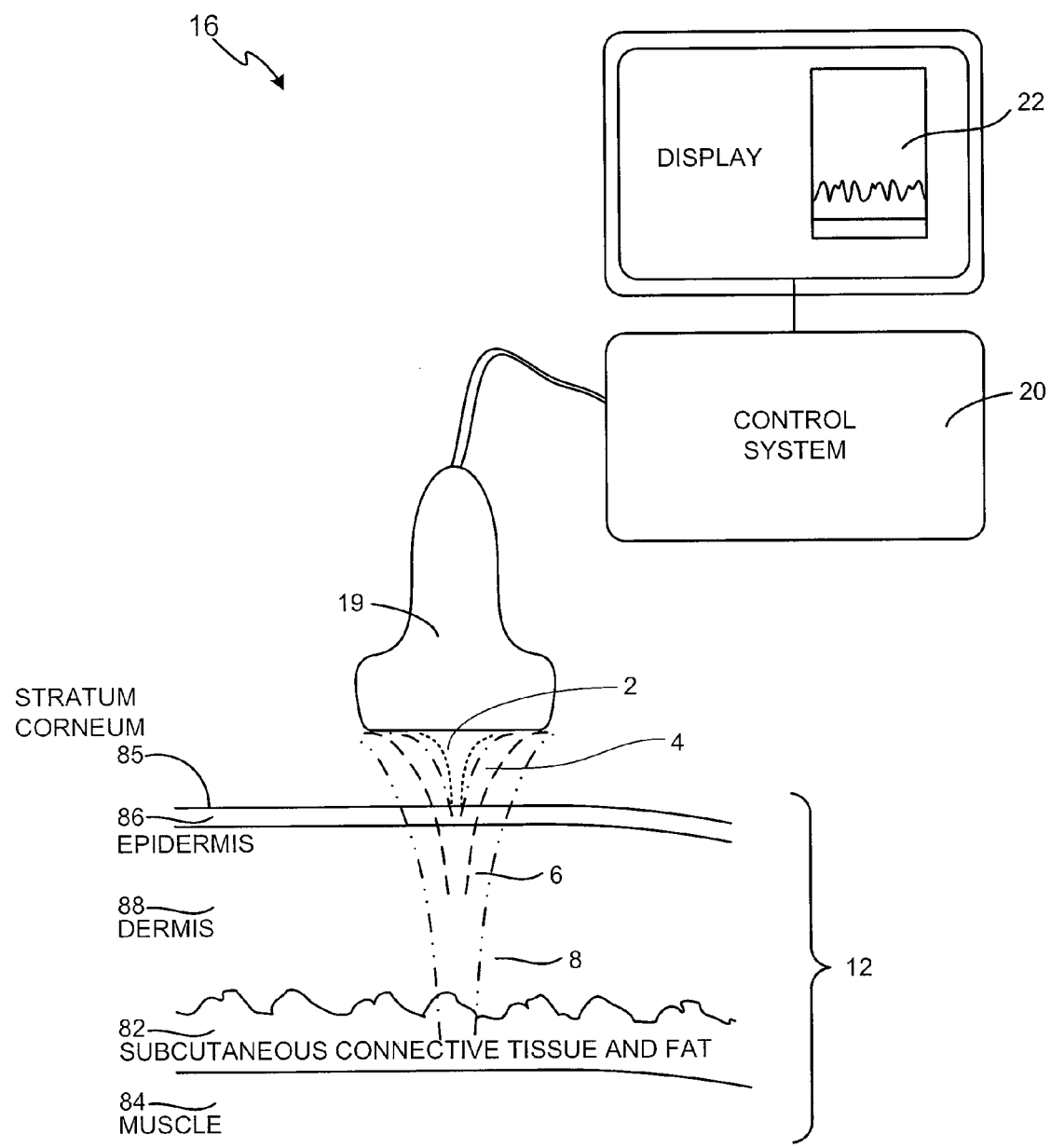
FIG. 3 illustrates a schematic diagram of a system for modulating medicants in accordance with an exemplary embodiment of the present invention.

In an exemplary embodiment, with reference to FIG. 3, an exemplary system 16, comprising a display 22, a control system 20, a transducer 19, is used to deliver energy 2, 4, 6, and/or 8 to and monitor ROI 12, within one or more of stratum corneum 85, viable epidermis 86, dermis 88, subcutaneous connective tissue and fat 82, and muscle 84. Other exemplary systems are disclosed in co-pending U.S. patent application Ser. No. 10/950,112 entitled "Method and System For Combined Ultrasound Treatment", which is hereby incorporated by reference.

With continued reference to FIG. 3, an exemplary transducer 19 is a transducer that delivers ultrasound energy 2, 4, 6 and/or 8 to ROI 12. In some embodiments, a fluid filled or gel couple is used to couple transducer 19 to a patient's body. In some embodiments, an additional coupling is necessary and/or multiple fluid filled or gel couples are used, each having distinct acoustic properties.

In another exemplary embodiment, suction is used to attach transducer 19 to the patient's body. In this exemplary embodiment, a negative pressure differential is created and transducer 19 attaches to stratum corneum 85 by suction. A vacuum-type device is used to create the suction and the vacuum device can be integral with, detachable, or completely separate from transducer 19. The suction attachment of transducer 19 to stratum corneum 85 and associated negative pressure differential ensures that transducer 19 is properly coupled to stratum corneum 85. Further, the suction-attachment also reduces the thickness of the tissue to make it easier to reach distinct layers of tissue.

With additional reference to FIG. 3, ultrasound energy 2, 4, 6 and/or 8 can be emitted in various energy fields. Energy fields can be focused, unfocused, defocused, and/or made substantially planar by transducer 19 to provide a plurality of different effects. Energy can be applied at one or more points in one or more C-planes or C-scans by automated or manual movement. For example, a substantially planar energy field can provide a therapeutic and/or pretreatment effect, a focused energy field can provide a more intense therapeutic effect, and a non-focused energy field can provide a more mild therapeutic effect. It should be noted that the term "non-focused" as used throughout, is meant to encompass energy that is unfocused or defocused.

An exemplary transducer 19 emits ultrasound energy for imaging, or treatment, or a combination of both imaging and treatment. In an exemplary embodiment, transducer 19 is configured to emit ultrasound energy at specific depths in ROI 12, as described below. In this exemplary embodiment of FIG. 3, transducer 19 emits unfocused or defocused ultrasound energy over a wide area in ROI 12 for treatment purposes.

Figure 4A:
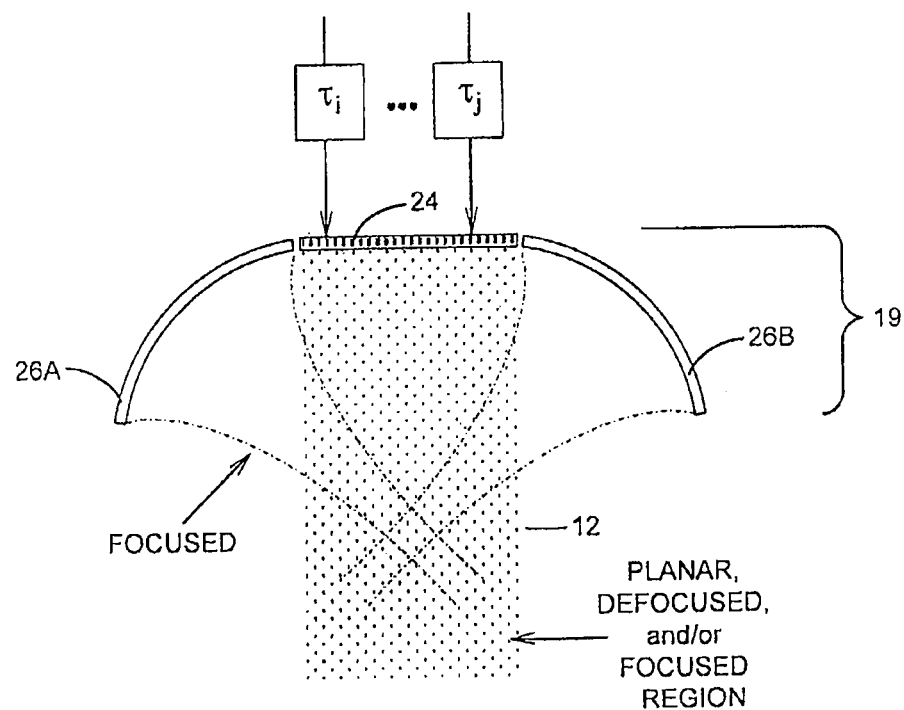
FIGS. 4A, 4B, 4C, 4D and 4E illustrate cross-sectional diagrams of an exemplary transducer in accordance with various embodiments of the present invention.
Figure 4B:
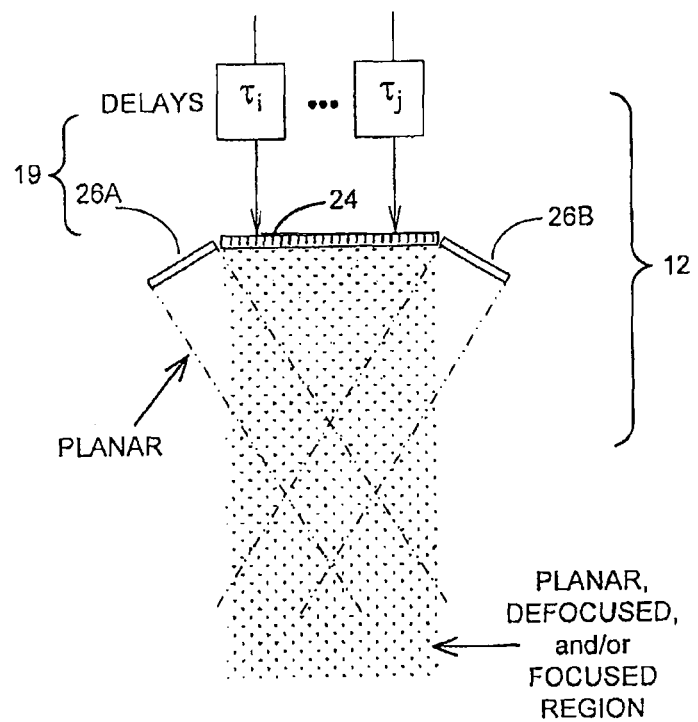

With reference to FIGS. 4A and 4B, transducer 19 can comprise one or more transducers configured for facilitating treatment. Transducer 19 can also comprise one or more transduction elements, e.g., elements 26A or 26B. The transduction elements can comprise a piezoelectrically active material, such as lead zirconante titanate (PZT), or any other piezoelectrically active material, such as a piezoelectric ceramic, crystal, plastic, and/or composite material, as well as lithium niobate, lead titanate, barium titanate, and/or lead metaniobate. In addition to, or instead of a piezoelectrically active material, transducer 19 can comprise any other materials configured for generating radiation and/or acoustical energy. Transducer 19 can also comprise one or more matching and/or backing layers configured along with the transduction elements such as coupled to the piezoelectrically active material. Transducer 19 can also be configured with single or multiple damping elements along the transduction elements.

In accordance with an exemplary embodiment, the thickness of the transduction elements of transducer 19 can be configured to be uniform. That is, the transduction elements can be configured to have a thickness that is substantially the same throughout. In accordance with another exemplary embodiment, the transduction elements can also be configured with a variable thickness, and/or as a multiple damped device. For example, the transduction elements of transducer 19 can be configured to have a first thickness selected to provide a center operating frequency of a lower range, for example from approximately 1 kHz to 3 MHz. Transduction element 26 can be configured with a second thickness selected to provide a center operating frequency of a higher range, for example from approximately 3 to 100 MHz, or more.

Transducer 19 can be configured as a single broadband transducer excited with at least two or more frequencies to provide an adequate output for raising the temperature within ROI 12 to a desired level. Transducer 19 can also be configured as two or more individual transducers, wherein each transducer 19 comprises transduction elements, the thickness of which may be selected as above to provide a desired center operating frequency.

Moreover, in an exemplary embodiment, any variety of mechanical lenses or variable focus lenses, e.g. liquid-filled lenses, may also be used to additionally focus and or defocus the energy field. For example, with reference to exemplary embodiments depicted in FIGS. 4A and 4B, transducer 19 may also be configured with an electronic focusing array 24 in combination with one or more transduction elements to facilitate increased flexibility in treating ROI 12. Array 24 may be configured in a manner similar to transducer 19. That is, array 24 can be configured as an array of electronic apertures that may be operated by a variety of phases via variable electronic time delays, for example, $\tau_i \ldots \tau_j$. By the term "operated," the electronic apertures of array 24 may be manipulated, driven, used, and/or configured to produce and/or deliver energy in a manner corresponding to the phase variation caused by electronic time delays. For example, these phase variations can be used to deliver defocused beams, planar beams, and/or focused beams, each of which may be used in combination to achieve different physiological effects in ROI 12.

Transduction elements may be configured to be concave, convex, and/or planar. For example, in an exemplary embodiment depicted in FIG. 4A, transduction elements 26A and 26B are configured to be concave in order to provide focused energy for treatment of ROI 12. Additional embodiments are disclosed in U.S. patent application Ser. No. 10/944,500, entitled "System and Method for Variable Depth Ultrasound Treatment", incorporated herein by reference. In an exemplary embodiment of FIG. 4A transduction elements 24 and associated time or phase delays are perpendicular to that shown in FIG. 4A, whereby such perpendicularly disposed transduction elements 24 are therapy, imaging, or dual-mode imaging-therapy elements.

In another exemplary embodiment, depicted in FIG. 4B, transduction elements 26A and 26B can be configured to be substantially flat in order to provide substantially uniform energy to ROI 12. In an exemplary embodiment of FIG. 4B transduction elements 24 and associated time or phase delays are perpendicular to that shown in FIG. 4B, whereby such perpendicularly disposed transduction elements 24 are therapy, imaging, or dual-mode imaging-therapy elements. While FIGS. 4A and 4B depict exemplary embodiments with the transduction elements configured as concave and substantially flat, respectively, the transduction elements can be configured to be concave, convex, and/or substantially flat. In addition, the transduction elements can be configured to be any combination of concave, convex, and/or substantially flat structures. For example, a first transduction element can be configured to be concave, while a second transduction element within transducer 19 can be configured to be substantially flat.

Figure 4C:
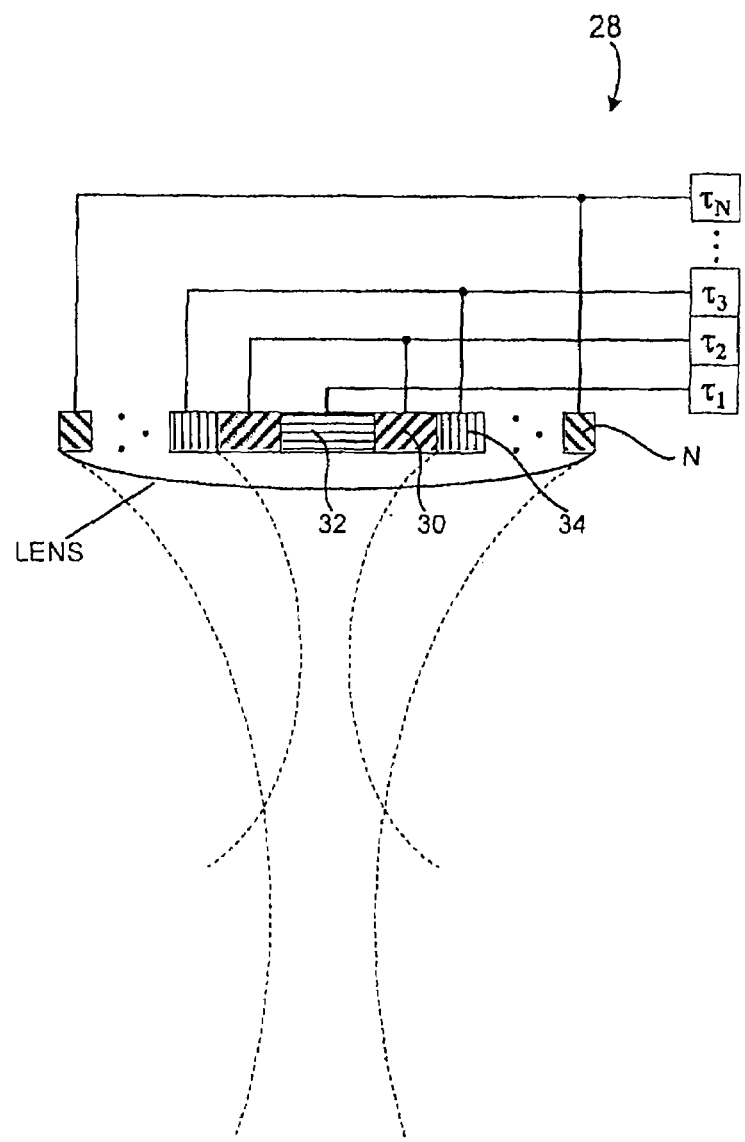
Figure 4D:
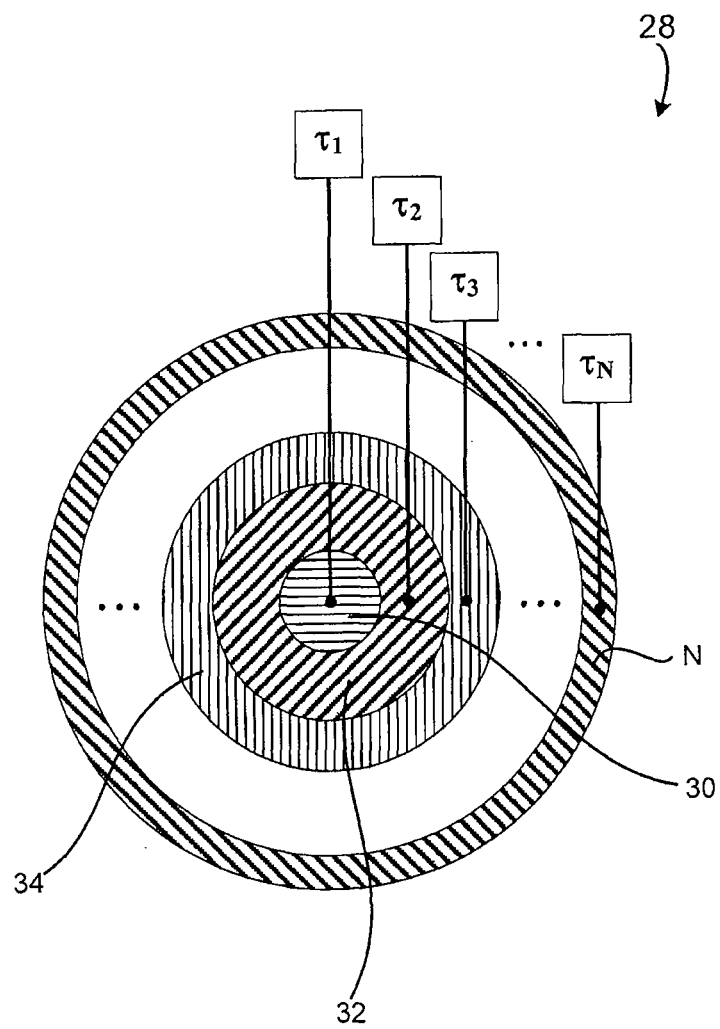

With reference to FIGS. 4C and 4D, transducer 19 can also be configured as an annular array to provide planar, focused and/or non-focused acoustical energy. For example, in accordance with an exemplary embodiment, an annular array 28 can comprise a plurality of rings 30, 32, 34 to N. Rings 30, 32, 34 to N can be mechanically and electrically isolated into a set of individual elements, and can create planar, focused, or non-focused waves. For example, such waves can be centered on-axis, such as by methods of adjusting corresponding transmit and/or receive delays, $\tau_1, \tau_2, \tau_3 \ldots \tau_N$. An electronic focus can be suitably moved along various depth positions, and can enable variable strength or beam tightness, while an electronic defocus can have varying amounts of defocusing. In accordance with an exemplary embodiment, a lens and/or concave, convex, and/or substantially flat shaped annular array 28 can also be provided to aid focusing or defocusing such that any time differential delays can be reduced. Movement of annular array 28 in one, two or three-dimensions, or along any path, such as through use of probes and/or any conventional robotic arm mechanisms, may be implemented to scan and/or treat a volume or any corresponding space within ROI 12.

Figure 4E:
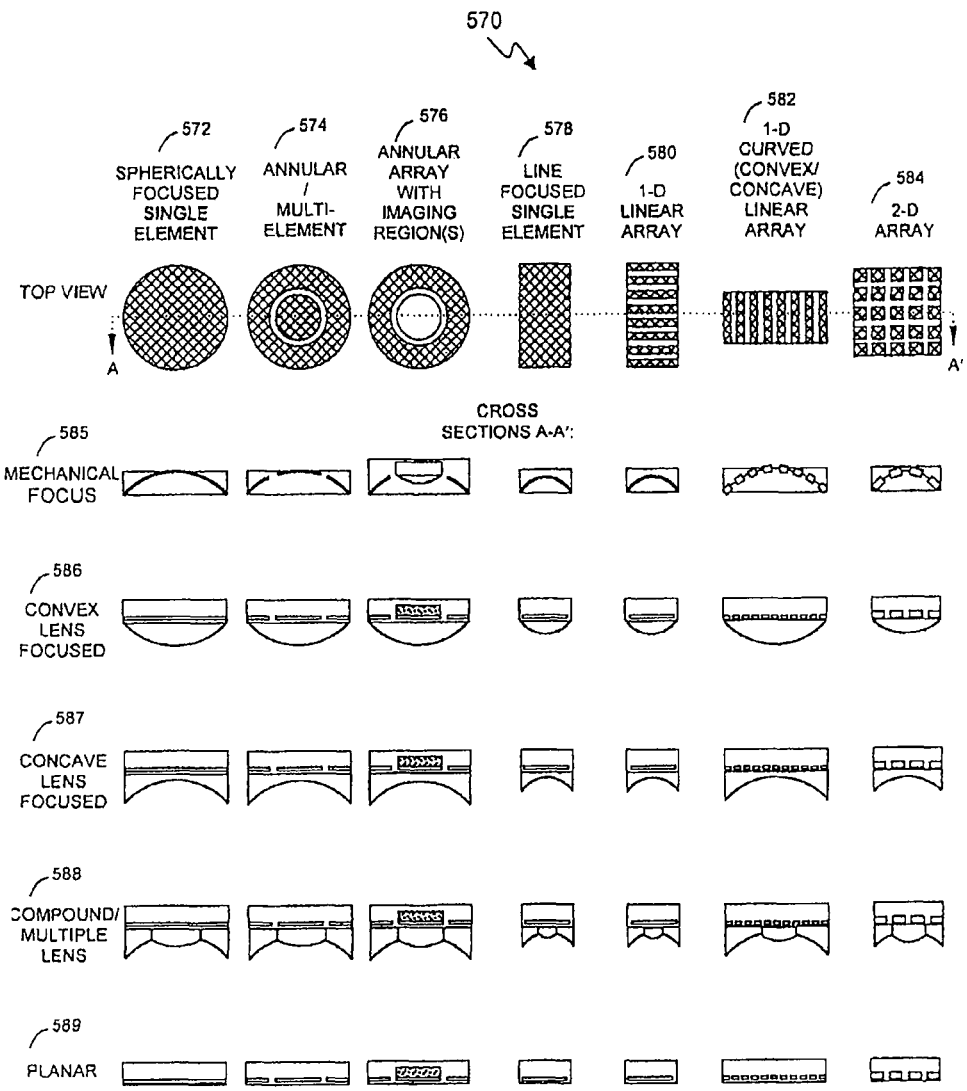

With reference to FIG. 4E, an exemplary transducer 570 can also be configured as a spherically focused single element 572, annular/multi-element 574, annular array with imaging region(s) 576, line focused single element 578, 1-D linear array 580, 1-D curved (convex/concave) linear array 582, and/or 2-D array 584, with mechanical focus 585, convex lens focus 586, concave lens focus 587, compound/multiple lens focus 588, and/or planar array form 589, to achieve focused, unfocused, or non-focused sound fields for both imaging and/or therapy. Other lens shapes can still be used in other exemplary embodiments of the present invention. Analogous to spherically focused single element 572 to be configured for multiple annulii 574 and/or imaging regions 576, an exemplary embodiment for the therapeutic line-focused single element 578, and 1-D and 2-D arrays 580, 582 and 584 is to dispose one or more imaging elements or imaging arrays in their aperture, such as along the center of their aperture. In general a combination of imaging and therapy transducers or dual mode imaging-therapy transducers can be utilized.

Figure 5A:
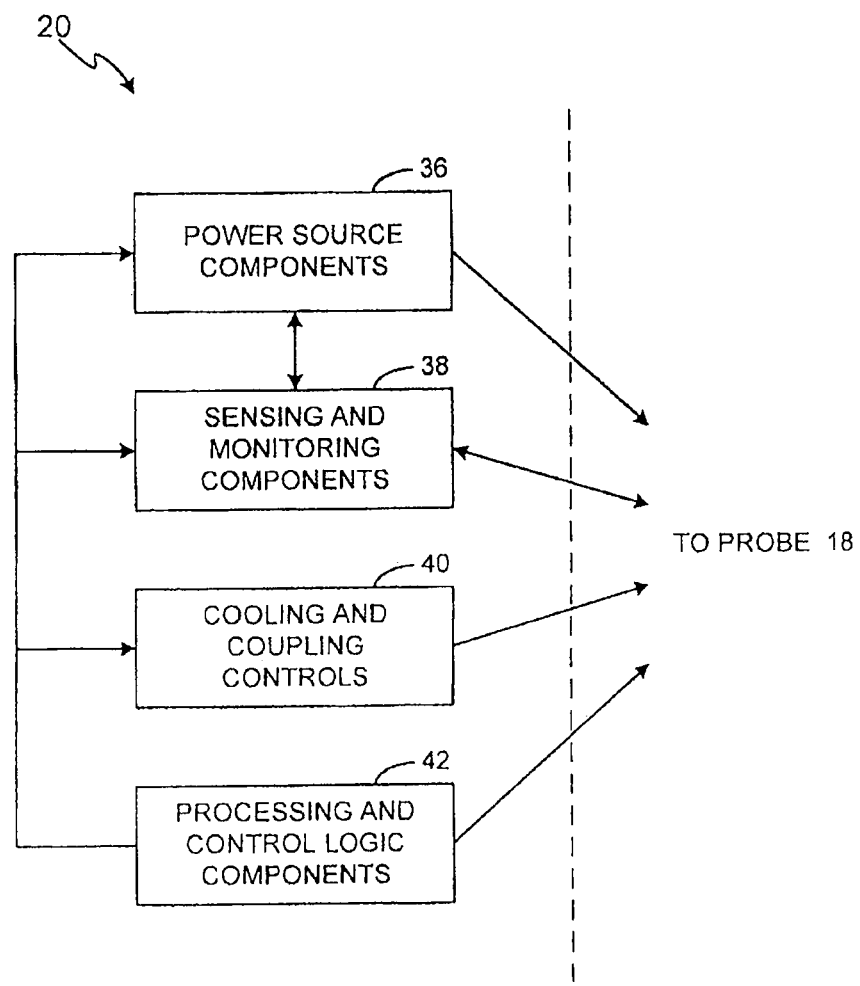
FIGS. 5A, 5B, and 5C illustrate block diagrams of an exemplary control system in accordance with exemplary embodiments of the present invention.
Figure 5B:
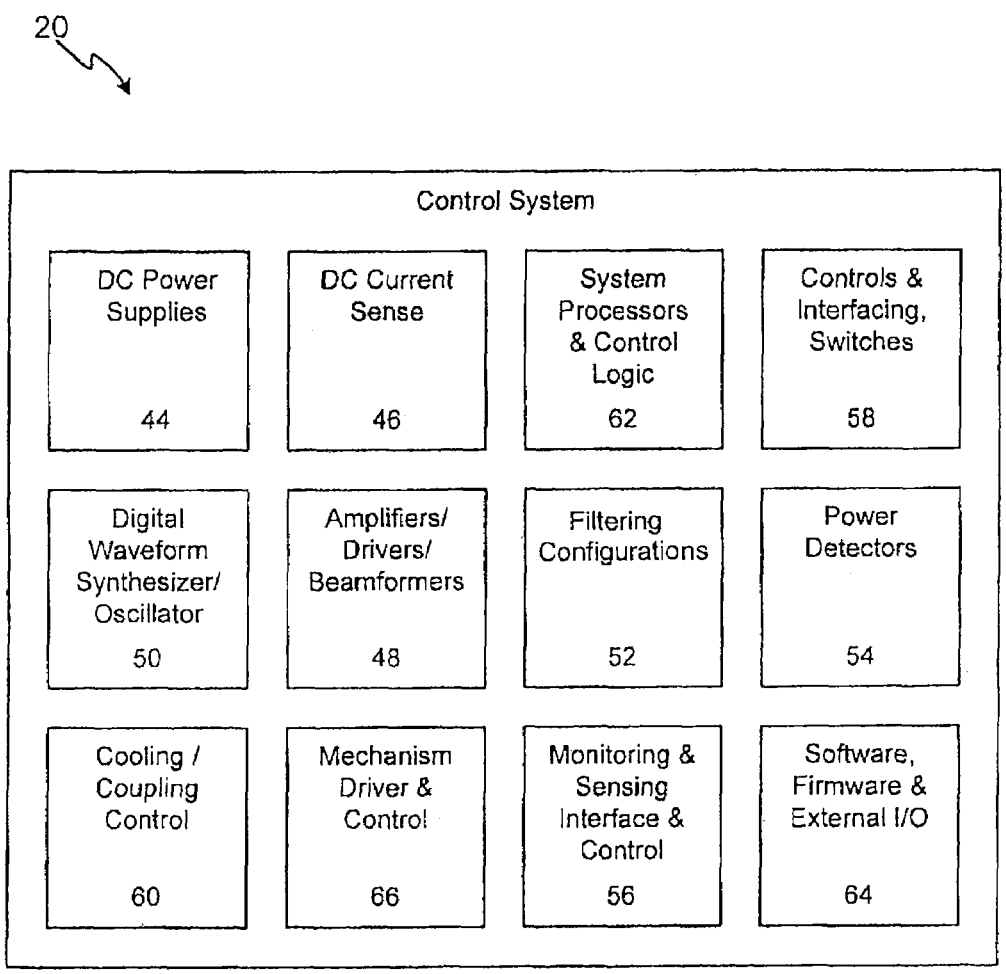

An exemplary transducer is suitably controlled and operated in various manners by control system 20. In an exemplary embodiment depicted in FIGS. 5A-5C, control system 20 is configured for coordination and control of the entire acoustic energy system. For example, control system 20 can suitably comprise power source components 36, sensing and monitoring components 38, cooling and coupling controls 40, and/or processing and control logic components 42. Control system 20 can be configured and optimized in a variety of ways with more or less subsystems and components to enhance therapy, imaging and/or monitoring, and the embodiments in FIGS. 5A and 5B are merely for illustration purposes.

For example, for power sourcing components 36, control system 20 can comprise one or more direct current (DC) power supplies 44 configured to provide electrical energy for entire control system 20, including power required by a transducer electronic amplifier/driver 48. A DC current sense device 46 can also be provided to confirm the level of power going into amplifiers/drivers 48 for safety and monitoring purposes.

Amplifiers/drivers 48 can comprise multi-channel or single channel power amplifiers and/or drivers. In accordance with an exemplary embodiment for transducer array configurations, amplifiers/drivers 48 can also be configured with a beamformer to facilitate array focusing. An exemplary beamformer can be electrically excited by a digitally controlled waveform synthesizer/oscillator 50 with related switching logic.

Power sourcing components 36 can also include various filtering configurations 52. For example, switchable harmonic filters and/or matching may be used at the output of amplifier/driver/beamformer 48 to increase the drive efficiency and effectiveness. Power detection components 54 may also be included to confirm appropriate operation and calibration. For example, electric power and other power detection components 54 may be used to monitor the amount of power going to probe 18.

Various sensing and monitoring components 38 may also be suitably implemented within control system 20. For example, in accordance with an exemplary embodiment, monitoring, sensing, interface and control components 56 may be configured to operate with various motion detection systems implemented within transducer 19 to receive and process information such as acoustic or other spatial and/or temporal information from ROI 12. Sensing and monitoring components 38 can also include various controls, interfacing and switches 58 and/or power detectors 54. Such sensing and monitoring components 38 can facilitate open-loop and/or closed-loop feedback systems within treatment system 14.

In an exemplary embodiment, sensing and monitoring components 38 comprise a sensor that is connected to an audio or visual alarm system to prevent overuse of system 14. In this exemplary embodiment, the sensor senses the amount of energy transferred to stratum corneum 85, viable epidermis 86, viable dermis 88, subcutaneous connective tissue and fat 82, or muscle 84, or the time that system 14 has been actively emitting energy. When a certain time or temperature threshold has been reached, the alarm sounds an audible alarm or causes a visual indicator to activate to alert the user that the threshold is reached. This prevents the user from overusing system 14. In an exemplary embodiment, the sensor could be operatively connected to control system 20 and force control system 20 to stop emitting ultrasound energy 2, 4, 6 and/or 8 from probe 18.

A cooling/coupling control system 60 may be provided to remove waste heat from an exemplary probe 18, provide a controlled temperature at the superficial tissue interface and deeper into tissue, and/or provide acoustic coupling from probe 18 to ROI 12. Such cooling/coupling control system 60 can also be configured to operate in both open-loop and/or closed-loop feedback arrangements with various coupling and feedback components.

Additionally, an exemplary control system 20 can further comprise various system processors and digital control logic 62, such as one or more controls or interfacing switches 58 and associated components, including firmware and software 64, which interfaces to user controls and interfacing circuits as well as input/output circuits and systems for communications, displays, interfacing, storage, documentation, and other useful functions. Software 64 controls all initialization, timing, level setting, monitoring, safety monitoring, and all other system functions required to accomplish user-defined treatment objectives. Further, various mechanisms 66 can also be suitably configured to control operation.

Figure 5C:
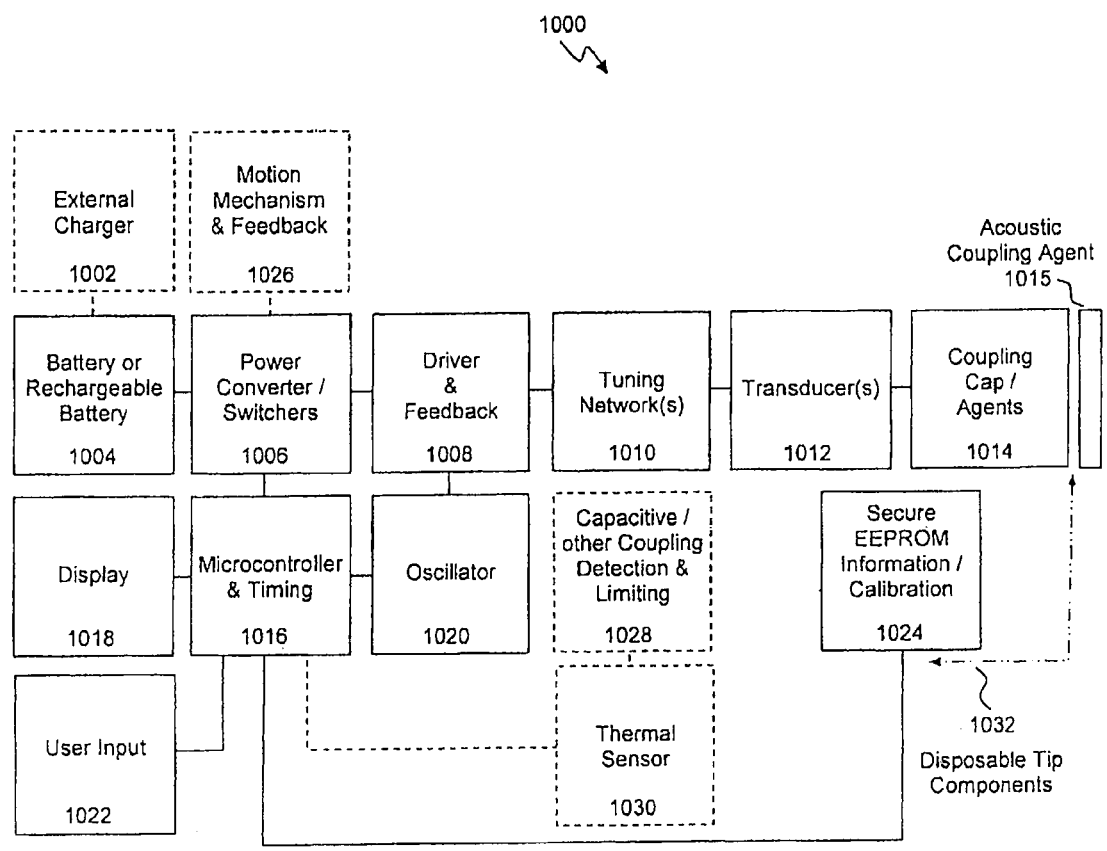

With reference to FIG. 5C, an exemplary transducer is suitably controlled and operated in various manners by a hand-held format control system 1000. An external battery charger 1002 can be used with rechargeable-type batteries 1004 or batteries 1004 can be single-use disposable types, such as AA-sized cells. Power converters 1006 produce voltages suitable for powering a driver/feedback circuit 1008 with tuning network 1010 driving a transducer 1012 coupled to the patient via one or more fluid filled or gel couples. In some embodiments, a fluid filled or gel couple is coupled to the patient with an acoustic coupling agent 1015. In addition, a microcontroller and timing circuits 1016 with associated software and algorithms provide control and user interfacing via a display 1018, oscillator 1020, and other input/output controls 1022 such as switches and audio devices. A storage element 1024, such as an EEPROM, secure EEPROM, tamper-proof EEPROM, or similar device holds calibration and usage data. A motion mechanism with feedback 1026 can be suitably controlled to scan the transducer, if desirable, in a line or two-dimensional pattern and/or with variable depth. Other feedback controls include a capacitive, acoustic, or other coupling detection means and/or limiting controls 1028 and thermal sensor 1030. A combination of the secure EEPROM with at least one of a fluid filled or gel couple, transducer 1012, thermal sensor 1030, coupling detectors 1028, or tuning network 1010 along with a plastic or other housing can comprise a disposable tip 1032.

With reference again to FIG. 3, an exemplary system 14 also includes display system 22 to provide images of the ROI 12 in certain exemplary embodiments wherein ultrasound energy is emitted from transducer 19 in a manner suitable for imaging. Display system can be any type of system that conveys images or information apart from images about system 14 or ROI 12 to the user. Therefore, display system 22 can be a computer monitor, television screen or it can be a simply type of indicator system such a liquid crystal display or light emitting diode display in various exemplary embodiments. Liquid crystal displays and light emitting diode displays are particularly useful when system 14 is a hand-held system.

Display system 22 enables the user to facilitate localization of the treatment area and surrounding structures, e.g., identification of cell membranes or tissues. After localization, delivery of ultrasound energy 2, 4, 6 and/or 8 at a depth, distribution, timing, and energy level is provided, to achieve the desired therapy, imaging and/or monitoring. Before, during, and/or after therapy, i.e., before, during and/or after delivery of ultrasound energy, monitoring of the treatment area and surrounding structures can be conducted to further plan and assess the results and/or provide feedback to control system 20 and a system operator via display system 22. In accordance with an exemplary embodiment, localization can be facilitated through ultrasound imaging that can be used to define an ROI 12 within one or more layers of skin tissue.

For ultrasound energy delivery, transducer 19 can be mechanically and/or electronically scanned to place treatment zones over an extended area in ROI 12. A treatment depth can be adjusted between a range of approximately 1 to 100 millimeters, and/or the greatest depth of muscle 84. Such delivery of energy can occur through imaging of the targeted cell membrane or tissue and then applying ultrasound energy, or application of ultrasound energy at known depths over an extended area without initial or ongoing imaging.

The ultrasound beam from transducer 19 can be spatially and/or temporally controlled by changing the spatial parameters of transducer 19, such as the placement, distance, treatment depth and transducer 19 structure, as well as by changing the temporal parameters of transducer 19, such as the frequency, drive amplitude, and timing, with such control handled via control system 20. Such spatial and temporal parameters can also be suitably monitored and/or utilized in open-loop and/or closed-loop feedback systems within ultrasound system 16.

In accordance with another exemplary embodiment of the present invention, with reference again to FIG. 3, an exemplary monitoring method may comprise monitoring the temperature profile or other tissue parameters of ROI 12, such as attenuation, speed of sound, or mechanical properties such as stiffness and strain of the treatment region and suitably adjust the spatial and/or temporal characteristics and energy levels of ultrasound energy 2, 4, 6 and/or 8 emitted from transducer 19. The results of such monitoring techniques may be indicated on display system 22 by means of one-, two-, or three-dimensional images of monitoring results, or may simply comprise a success or fail-type indicator, or combinations thereof. Additional treatment monitoring techniques may be based on one or more of temperature, video, profilometry, and/or stiffness or strain gauges or any other suitable sensing technique.

Any amount of energy can be used as long as the tissue within ROI 12 is not ablated or coagulated. In an exemplary embodiment, the energy emitted from probe 18 is unfocused or defocused ultrasound energy 2, 4, 6 and/or 8. Alternatively, focused ultrasound energy 2, 4, 6 and/or 8 could be emitted from probe 18 and applied to ROI 12.

In certain exemplary embodiments, system 14 is equipped with certain features to aid the user. One feature is a disposable tip that covers probe 18 during use. The disposable tip enables ultrasound energy 2, 4, 6, and/or 8 to pass through the tip and contact the patient. But, the disposable tip can be removed from probe 18 after use and replaced with a new disposable tip to prevent the spread of germs from one patient to another that might reside on probe 18 after contact with a patient's stratum corneum 85. Different size disposable tips can be used and fall within the scope of the present invention.

In one exemplary embodiment, the energy released into ROI 12 increases the local temperature within ROI 12 from approximately 1°-25° C. over a body's normal temperature. Therefore the temperature within ROI 12 during treatment is between approximately 35°-60° C. In another exemplary embodiment, the temperature is raised approximately 1°-15° C. over a body's normal temperature. Therefore, in this embodiment, the temperature within ROI 12 is between approximately 35°-49° C. While specific temperature ranges are disclosed herein, it should be noted that any temperature is considered to fall within the scope of the present invention.

In certain embodiments, the temperature increase may be very high but applied for a short enough time period so that the energy delivered to ROI 12 does not cause tissue ablation or coagulation. In other situations, the temperature increase may be fairly small and applied long enough to have an effect without causing tissue ablation or coagulation.

The time-temperature profile can be modeled and optimized with the aid of the thermal dose concept. The thermal dose, or $t_{43}$, is the exposure time at 43° C. which causes an equivalent biological effect due to an arbitrary time-temperature heating profile. Typically an ablative lesion forms on the order of one second at 56° C., which corresponds to a thermal dose of one hundred and twenty minutes at 43° C. The same thermal dose corresponds to 50° C. for approximately one minute. Thus a non-ablative profile can contain high temperatures for very short times and/or lower temperatures for longer times or a combination of various time-temperature profiles. For example, temperatures as high as 56° C. for under one second or 46° C. for under fifteen minutes can be utilized. Such processes can be implemented in various exemplary embodiments, whereby one or more profiles may be combined into a single treatment.

In an exemplary embodiment the temperature at ROI 12 is raised to a high level, such as approximately 50° C. or more and held for several seconds. In another exemplary embodiment, the temperature is raised to a high level, (for example greater than 50° C.), for under one second up to five seconds or more, and then turned off for under one second up to five seconds or more, and repeated to create a pulsed profile.

In another exemplary embodiment, the temperature is raised quickly to a high level (greater than 50° C.), and then dropped to a lower temperature (less than 50° C.), and then maintained at that temperature for a given time period such as one second up to several seconds or over a minute.

In another exemplary embodiment, the temperature is increased quickly to a high level ($T_{HIGH}$), whereby $T_{HIGH}$ is greater than 40° C., and the power to system 14 is turned off, but turned on again once the temperature drops below a lower threshold, ($T_{LOW}$), whereby $T_{LOW}$ is less than $T_{HIGH}$. Once the temperature reaches $T_{HIGH}$ again power to system 14 is turned back off and this process is repeated, in effect acting like a thermostat. The process is terminated after a total treatment time of under one second to one minute or more.

In another exemplary embodiment, the temperature is raised quickly to a high level ($T_{START}$), whereby $T_{START}$ is greater than 40° C. and then turned off, but turned on again before the temperature drops appreciably (i.e. by a few degrees) below $T_{START}$, whereby the temperature may then increase a small amount (i.e. by a few degrees) over $T_{START}$ before the power is turned off again. In such an exemplary embodiment the temperature quickly reaches a starting point and then may be allowed to increase to a higher temperature yet still remain in a non-ablative or coagulative regime before the treatment is ended.

The present invention may be described herein in terms of various functional components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical contexts and that the exemplary embodiments relating to a system as described herein are merely indicative of exemplary applications for the invention. For example, the principles, features and methods discussed may be applied to any medical application. Further, various aspects of the present invention may be suitably applied to other applications, such as other medical or industrial applications.

We claim:

1. A method for steering a medicant through a tissue, the tissue having a first region located at a first depth and a second region adjacent to the first region and located at a second depth, the method comprising the steps of:

presenting a medicant to the first region of the tissue;

focusing, using a source of ultrasound energy, a first acoustic energy from the source to the first region, the first acoustic energy having a first spatial and temporal energy profile configured to provide cavitation and radiation force, thereby initiating cavitation and radiation force, thereby moving the medicant from the first region to the second region;

focusing, using the source of ultrasound energy, a second acoustic energy from the source to the second region, the second acoustic energy having a second spatial and temporal energy profile configured to enhance effectiveness of the medicant, thereby enhancing the effectiveness of the medicant in the second region.

2. The method of claim 1, further comprising the step of coupling said source to said tissue with a coupling agent, wherein said coupling agent comprises said medicant.

3. The method of claim 1, wherein said medicant is a chemical naturally occurring within the body.

4. The method of claim 3, wherein said chemical is selected from the group consisting of a cell, an amino acid, a protein, an antibody, a mineral, and a vitamin.

5. The method of claim 1, wherein enhancing the effectiveness of the medicant comprises increasing permeability or transparency of said medicant in said tissue with said second acoustic energy.

6. The method of claim 1, wherein said presenting a medicant to the first region of the tissue comprises diffusing the medicant into the first region of the tissue.

7. The method of claim 1, wherein said presenting a medicant to a tissue comprises administering said medicant into at least a portion of a circulatory system in contact with said tissue.

8. The method of claim 1, wherein said presenting a medicant to a tissue comprises injecting said medicant into a portion of said tissue.

9. The method of claim 1, wherein enhancing the effectiveness of the medicant comprises creating a thermal effect in said tissue with said second acoustic energy.

10. A method for delivering a medicant to a region of interest within a tissue, the tissue having a first region located at a first depth, the region of interest located adjacent to the first region and at a second depth, the method comprising the steps of:

coupling an ultrasound probe to the tissue, the ultrasound probe configured to focus acoustic energy into the first region and the region of interest;

presenting a medicant to the first region of the tissue;

focusing, using the probe, a first acoustic energy to the first region, wherein said first acoustic energy has a first spatial and temporal energy profile configured to provide cavitation and radiation force in the first region that moves the medicant from the first region to the region of interest, thereby creating cavitation and radiation force in the first region and moving the medicant from the first region to the region of interest; and focusing, using the probe, a second acoustic energy to the region of interest, wherein the second acoustic energy has a second spatial and temporal energy profile configured to provide a thermal effect in the region of interest that enhances the effectiveness of the medicant, thereby creating the thermal effect in the region of interest and enhancing the effectiveness of the medicant.

11. A method for delivering a medicant to a portion of skin beneath a stratum corneum, the method comprising:

applying a medicant to a surface of the portion of skin stratum corneum;

coupling an ultrasound source to the medicant and the portion of skin;

focusing a first acoustic energy emitted by the ultrasound source to a first depth beneath the stratum corneum, wherein the first acoustic energy has a first spatial and temporal energy profile configured to provide cavitation and radiation force, thereby delivering the medicant across the stratum corneum to the first depth beneath the stratum corneum; and focusing a second acoustic energy emitted by the ultrasound source into a second depth beneath the stratum corneum, wherein the second acoustic energy has a second spatial and temporal energy profile configured to provide cavitation and radiation force, thereby delivering the medicant from the first depth to the second depth beneath the stratum corneum, wherein the first acoustic energy is different than the second acoustic energy.

12. The method of claim 11 the method further comprising:

focusing a third acoustic energy to the second depth beneath the stratum corneum, wherein the third acoustic energy has a third spatial and temporal energy profile configured to activate the medicant, thereby activating the medicant at the second depth, wherein the third acoustic energy is different than the first acoustic energy or the second acoustic energy.

13. The method of claim 12, wherein activating the medicant comprises creating a thermal effect in said tissue with said third acoustic energy from said source.

* * * * *